United States Patent
Inukai et al.

(10) Patent No.: US 8,023,848 B2
(45) Date of Patent: *Sep. 20, 2011

(54) DENSITY MEASURING DEVICE, LIQUID DEVELOPER STORING APPARATUS, AND IMAGE FORMING APPARATUS

(75) Inventors: Teruyuki Inukai, Matsumoto (JP); Toru Tanjo, Shiojiri (JP); Tsutomu Sasaki, Matsumoto (JP); Ken Ikuma, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 504 days.

This patent is subject to a terminal disclaimer.

(21) Appl. No.: 12/196,183

(22) Filed: Aug. 21, 2008

(65) Prior Publication Data

US 2009/0052946 A1 Feb. 26, 2009

(30) Foreign Application Priority Data

Aug. 24, 2007 (JP) ................................ 2007-217848
Jun. 26, 2008 (JP) ................................ 2008-167192

(51) Int. Cl.
  *G03G 15/10* (2006.01)
(52) U.S. Cl. .......................................... 399/64; 399/58
(58) Field of Classification Search .................. 399/57, 399/58, 61, 62, 64, 120, 359
See application file for complete search history.

(56) References Cited

U.S. PATENT DOCUMENTS

| 4,744,808 A | 5/1988 | Treu |
| 4,955,231 A | 9/1990 | Mahoney |

(Continued)

FOREIGN PATENT DOCUMENTS

JP          4080780 A       3/1992

(Continued)

OTHER PUBLICATIONS

Machine translation of reference Oka et al. (JP 09-243,559 A), Pub date Sep. 19, 1997.*

(Continued)

*Primary Examiner* — David Gray
*Assistant Examiner* — Rodney Bonnette
(74) *Attorney, Agent, or Firm* — DLA Piper LLP (US)

(57) ABSTRACT

A density measuring device includes a moving member that can be moved in a liquid, a light emitting member and a light receiving member that receives light emitted by the light emitting member. A gap part in which the moving member is disposed in a path of light emitted from the light emitting member can be moved. A density measuring unit measures the density of the liquid based on the result of output of the light receiving member for a case where the moving member is located in the path of light emitted from the light emitting member and a case where the moving member is not located in the path of light emitted from the light emitting member.

13 Claims, 21 Drawing Sheets

U.S. PATENT DOCUMENTS

| | | | |
|---|---|---|---|
| 5,156,048 A | 10/1992 | DeFigueiredo et al. | |
| 5,724,629 A * | 3/1998 | Iino et al. | 399/57 |
| 5,960,231 A | 9/1999 | Martinez | |
| 5,991,559 A | 11/1999 | Suetsugu et al. | |
| 6,278,850 B1 * | 8/2001 | Park | 399/57 |
| 6,603,934 B2 | 8/2003 | Shimmura | |
| 6,687,477 B2 * | 2/2004 | Ichida et al. | 399/237 |
| 6,694,112 B2 | 2/2004 | Sasaki et al. | |
| 6,876,822 B2 * | 4/2005 | Sasaki et al. | 399/57 |
| 7,004,650 B2 | 2/2006 | Sasaki et al. | |
| 7,231,821 B2 | 6/2007 | Fling et al. | |
| 7,778,576 B2 * | 8/2010 | Tanjo et al. | 399/238 |
| 7,885,565 B2 * | 2/2011 | Sasaki et al. | 399/57 |
| 2003/0016962 A1 * | 1/2003 | Teraoka et al. | 399/57 |
| 2003/0175049 A1 | 9/2003 | Ichida et al. | |
| 2004/0197116 A1 | 10/2004 | Yoshino et al. | |
| 2009/0053407 A1 * | 2/2009 | Inukai et al. | 427/145 |
| 2009/0060546 A1 * | 3/2009 | Tanaka et al. | 399/57 |
| 2009/0110424 A1 * | 4/2009 | Tanaka et al. | 399/57 |

FOREIGN PATENT DOCUMENTS

| | | |
|---|---|---|
| JP | 2000-249653 | 9/2000 |
| JP | 2002014541 A | 1/2002 |

OTHER PUBLICATIONS

Co-Pending U.S. Appl. No. 12/196,193.*
Co-Pending U.S. Appl. No. 12/196,397.*

* cited by examiner

DENSITY MEASURING DEVICE, LIQUID DEVELOPER STORING APPARATUS, AND IMAGE FORMING APPARATUS

CROSS-REFERENCE TO RELATED APPLICATIONS

This application claims the benefit of priority under 35 USC 119 of Japanese patent application no. 2007-217848, filed on Aug. 24, 2007, and Japanese patent application no. 2008-167192, filed on Jun. 26, 2008, which are hereby incorporated by reference.

BACKGROUND

1. Technical Field

The present invention relates to a density measuring device, a liquid developer storing apparatus, and an image forming apparatus capable of measuring the density of liquid toner acquired from dispersing toner into a carrier liquid.

2. Related Art

A liquid density detecting method is known that detects the density of a liquid in a broad range. In the method, a liquid as a target for density measurement is filled in concave parts that are formed in multi-level parts between an eccentric disc part and two disc parts in the circumferential direction by using a liquid carrying roller formed by integrally forming the eccentric disc part and two disc parts that have a same diameter larger than that of the eccentric disc and have the eccentric disc part interposed there between. Then, the liquid is formed to have a plurality of film thicknesses different from each other corresponding to the multi-levels, and the density of the liquid is detected based on the output of an optical sensor for the plurality of the film thicknesses (see JP-A-2000-249653).

However, in JP-A-2000-249653, at least two shafts of the disc parts and the eccentric disc part are needed, and a large space is required. In addition, a gap in the circumference is detected, thus an electrical process cannot be easily performed. In addition, the developer needs to be pumped from a storage unit by using a pump or the like, the number of constituent components is increased. In addition, since the density of the pumped developer is detected, the density is not identical to that of the developer inside the storage unit.

SUMMARY

An advantage of some aspects of the invention is that it provides a density measuring device, a liquid developer storing apparatus, and an image forming apparatus capable of precisely measuring the density of a liquid.

According to a first aspect of the invention, there is provided a density measuring device including: a moving member that can be moved in a liquid; a light emitting member; a light receiving member that receives light emitted by the light emitting member; a gap part in which the moving member disposed in a path of light emitted from the light emitting member can be moved; and a density measuring unit that measures the density of the liquid based on a result of output of the light receiving member for a case where the moving member is located in the path of light emitted from the light emitting member and a case where the moving member is not located in the path of light emitted from the light emitting member. According to the aspect above, the liquid does not need to be pumped to the density measuring unit by using a pump or the like, and the number of components is decreased. In addition, since the moving member is moved in the gap part, a new liquid can be inserted into the gap part, and accordingly, the precision of density measurement is improved.

The above-described density measuring device may be configured such that the light emitting member is disposed on a first side of the gap part and the light receiving member is disposed on a second side of the gap part. In such a case, the precision of density measurement is further improved.

The above-described density measuring device may be configured such that the light emitting member and the light receiving member are disposed on the first side of the gap part and a reflective member that reflects the light emitted from the light emitting member to the light receiving member is disposed on the second side of the gap part. In such a case, by disposing the light emitting member and the light receiving member on the same side, work efficiency is improved.

In the above-described density measuring device, the moving member may be configured to intermittently pass through the path of light emitted from the light emitting member. In such a case, density measurement can be performed more precisely.

In the above-described density measuring device, the moving member may be a rotary member. In such a case, the moving member can be moved in the gap part with a simple structure.

In the above-described density measuring device, the moving member may be in the shape of a rectangle. In such a case, a new liquid can be inserted into the gap part by using a simple structure.

The above-described density measuring device may further include an agitating member that has a same shaft as that of the moving member and agitates liquid developer. In such a case, the number of components can be decreased.

The above-described density measuring device may further include a first member that covers the light emitting member and is disposed on the first side; and a second member that covers the light receiving member, is formed separately from the first member, and is disposed on the second side. The gap part may be configured by the first member and the second member. In such a case, a measurement process appropriate for the type and state of the liquid can be performed.

The above-described density measuring device may further include a width adjusting member that adjusts the width of the gap part. In such a case, a measurement process more appropriate for the type and state of the liquid can be performed.

The above-described density measuring device may further include a second light receiving member that receives the light emitted from the light emitting member through a light path that does not pass through the moving member. In such a case, the precision of density measurement is further improved.

According to a second aspect of the invention, a liquid developer storing apparatus includes: a storage unit in which liquid developer is stored; and a density measuring device including: a moving member that can be moved in the storage unit; a light emitting member; a light receiving member that receives light emitted by the light emitting member; a gap part in which the moving member disposed in a path of light emitted from the light emitting member can be moved; and a density measuring unit that measures the density of the liquid based on the result of output of the light receiving member for a case where the moving member is located in the path of light emitted from the light emitting member and a case where the moving member is not located in the path of light emitted from the light emitting member. According to this aspect, the precision of density measurement is improved, and accordingly, the liquid developer can be precisely adjusted to a required density level.

According to a third aspect of the invention, an image forming apparatus includes: a developer container; a developer carrier that carries liquid developer; a developer supplying member that supplies the liquid developer stored in the developer container to the developer carrier; an image carrier on which a latent image is developed by the developer carrier; a transfer body that forms an image by transferring an image formed on the image carrier; a storage unit in which the liquid developer is stored; a developer collecting and supplying device that collects the liquid developer from the developer container into the storage unit and supplies the liquid developer and a carrier liquid; and a density measuring device including: a moving member that can be moved in the storage unit; a light emitting member; a light receiving member that receives light emitted by the light emitting member; a gap part in which the moving member disposed in a path of light emitted from the light emitting member can be moved; and a density measuring unit that measures the density of the liquid based on the result of output of the light receiving member for a case where the moving member is located in the path of light emitted from the light emitting member and a case where the moving member is not located in the path of light emitted from the light emitting member. According to this aspect, the precision of density measurement is improved, and accordingly, the liquid developer can be precisely adjusted to a required density level. Therefore an image with a high image quality can be formed.

The above-described image forming apparatus may further include a supply path through which the liquid developer is supplied from the storage unit of the liquid developer to the developer container. A wiring of the density measuring device is disposed along the supply path. In such a case, the number of components is decreased, and it is possible to maintain the wiring in a stable manner.

The above-described image forming apparatus may further include: a collecting path through which the liquid developer is collected into the storage unit of the liquid developer; an agitating propeller that agitates the liquid developer inside the storage unit of the liquid developer; and an agitating propeller shaft that supports the agitating propeller to be rotatable. The agitating propeller may overlap the collecting path, viewed from the direction of the agitating propeller shaft. According to this aspect, newly collected or supplied liquid developer can be agitated in a speedy manner.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
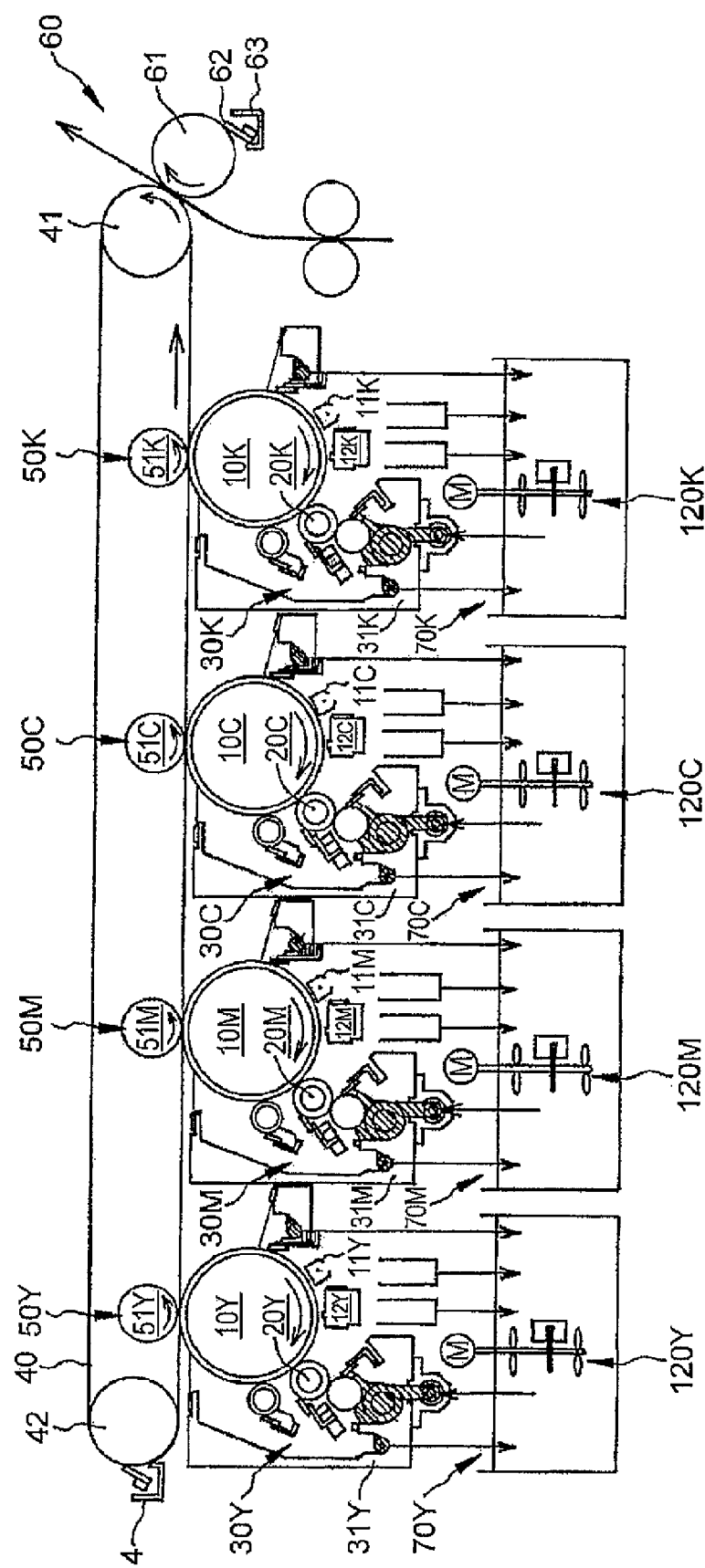
FIG. 1 is a diagram of an image forming apparatus according to an embodiment of the invention.

Hereinafter, an embodiment of the present invention will be described with reference to the accompanying drawings. FIG. 1 is a diagram showing major elements of an image forming apparatus according to an embodiment of the invention. Image forming units for each color are disposed in a center part of the image forming apparatus. Developing units 30Y, 30M, 30C, and 30K and developer collecting and supplying devices 70Y, 70M, 70C, and 70K are disposed in a lower part of the image forming apparatus. An intermediate transfer body 40 and a secondary transfer unit 60 are disposed in an upper part of the image forming apparatus.

The image forming units include image carriers 10Y, 10M, 10C, and 10K, corona chargings 11Y, 11M, 11C, and 11K, exposure units 12Y, 12M, 12C, and 12K, and the like. The exposure units 12Y, 12M, 12C, and 12K are constituted by line heads, in which LEDs or the like are aligned, and the like. The corona chargings 11Y, 11M, 11C, and 11K electrically charge the image carriers 11Y, 10M, 10C, and 10K, the exposure units 12Y, 12M, 12C, and 12K emit laser beams that have been modulated based on an input image signal, and electrostatic latent images are formed on the charged image carriers 10Y, 10M, 10C, and 10K.

The developing units 30Y, 30M, 30C, and 30K include developing rollers 20Y, 20M, 20C, and 20K, developer containers 31Y, 31M, 31C, and 31K that store liquid developers of colors including yellow Y, magenta M, cyan C, and black K, and developer supplying rollers 32Y, 32M, 32C, and 32K that supply the liquid developers of the colors from the developer containers 31Y, 31M, 31C, and 31K to the developing rollers 20Y, 20M, 20C, and 20K. The developing units 30Y, 30M, 30C, and 30K develop the electrostatic latent images formed on the image carriers 10Y, 10M, 10C, and 10K by using the liquid developers of the colors.

The intermediate transfer body 40 is an endless belt member that is tightly wound to extend between a driving roller 41 and a tension roller 42. While being brought into contact with the image carriers 10Y, 10M, 10C, and 10K by primary transfer units SOY, 50M, 50C, and 50K, the intermediate transfer body 40 is driven to rotate by the driving roller 41. Primary transfer rollers 51Y, 51M, 51C, and 51K of the primary transfer units 50Y, 50M, 50C, and 50K are disposed to face the image carriers 10Y, 10M, 10C, and 10K with the intermediate transfer body 40 interposed therebetween. The primary transfer units 50Y, 50M, 50C, and 50K sequentially transfer developed toner images of each color formed on the image carriers 10Y, 10M, 10C, and 10K on the intermediate transfer body 40 in a superposing manner by using contact positions between the image carriers 10Y, 10M, 10C, and 10K and the image carriers 10Y, 10M, 10C, and 10K as transfer positions, and thereby forming a full-color toner image.

A secondary transfer roller 61 of the secondary transfer unit 60 is disposed to face the belt driving roller 41 with the intermediate transfer body 40 interposed therebetween. In addition, a cleaning device including a secondary transfer roller cleaning blade 62 and a developer collecting unit 63 is disposed in the secondary transfer unit 60. The secondary transfer unit 60 transports and supplies a sheet member such as a paper sheet, a film, or a cloth to a sheet member transporting path L in accordance with a timing at which a full-color toner image formed by superposing colors on the intermediate transfer body 40 or a monochrome toner image arrives at the transfer position of the secondary transfer unit 60 and performs a secondary transfer process for the monochrome or full-color toner image on the sheet member. A fixing unit is disposed on the rear side of the sheet member transporting path L. By fusing and fixing the monochrome toner image or the full-color toner image transferred on the sheet member on a recording medium (sheet member) such as a paper sheet, an operation for forming a final image on the sheet member is completed.

On the side of the tension roller 42 that tightly supports the intermediate transfer body 40 together with the belt driving roller 41, a cleaning device including an intermediate transfer body cleaning blade 46 and a developer collecting unit 47 is disposed along the outer periphery of the tension roller 42. After passing through the secondary transfer unit 60, the intermediate transfer body 40 advances to a winding part of the tension roller 42. A cleaning operation for the intermediate transfer body 40 is then performed by the intermediate transfer body cleaning blade 46, and the intermediate transfer body 40 advances toward the primary transfer units 50 again.

The developer collecting and supplying devices 70Y, 70M, 70C, and 70K adjust the density of the liquid developer that has been collected from the image carriers 10Y, 10M, 10C, and 10K and the developing units 30Y, 30M, 30C, and 30K and supplies the liquid developer to the developer containers 31Y, 31M, 31C, and 31K.

Figure 2:
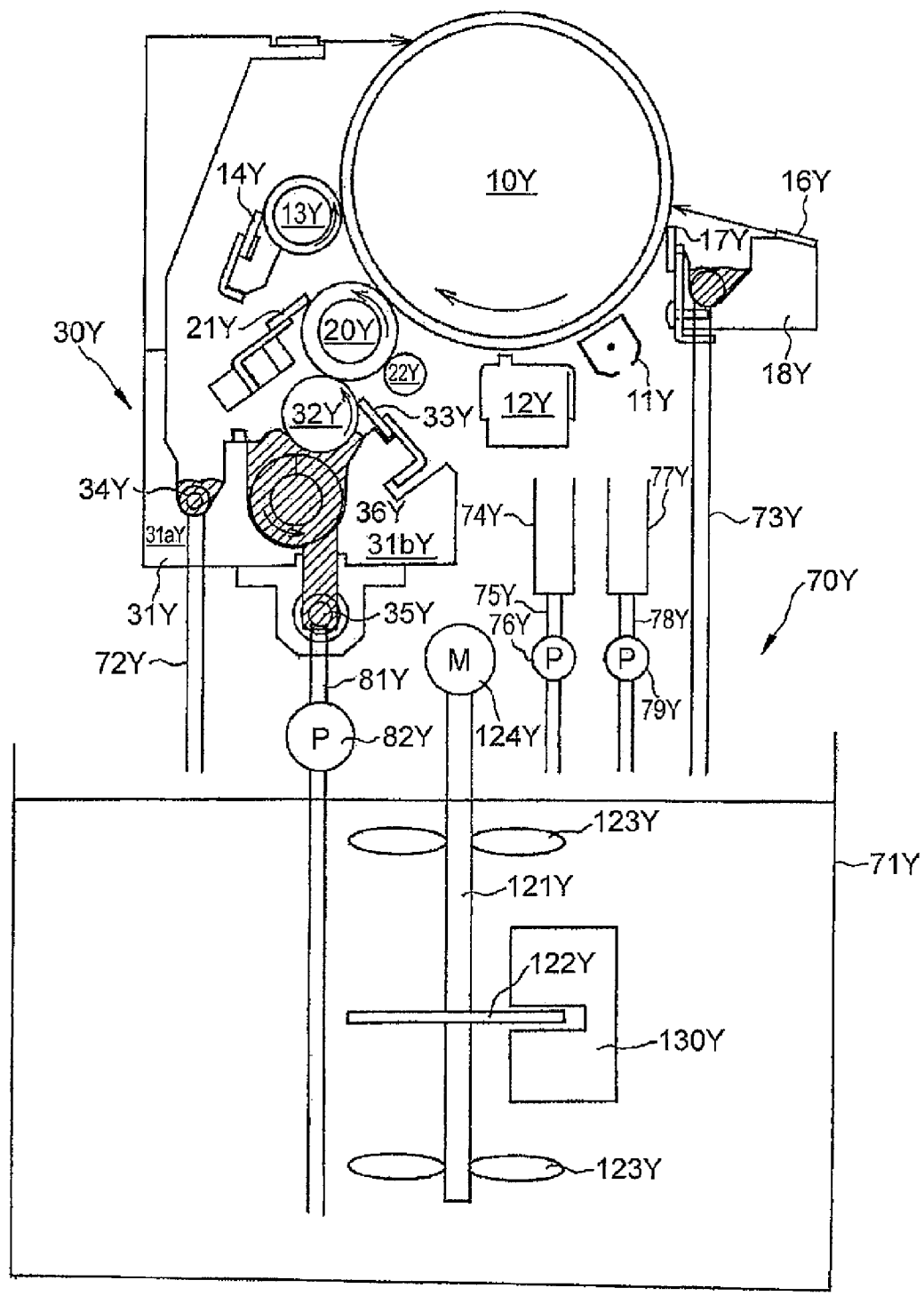
FIG. 2 is a cross-sectional view of major constituent elements of an image forming unit and a developing unit according to an embodiment of the invention.
Figure 3:
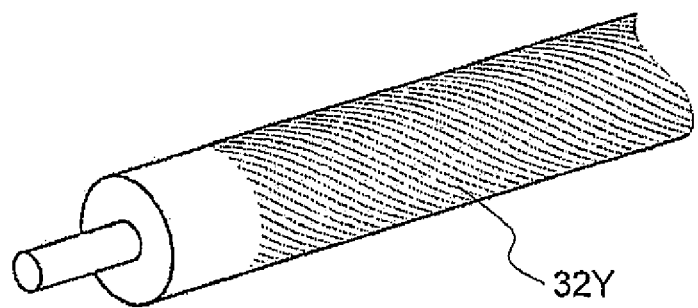
FIG. 3 is a perspective view of a developer supplying member according to an embodiment of the invention.
Figure 4:
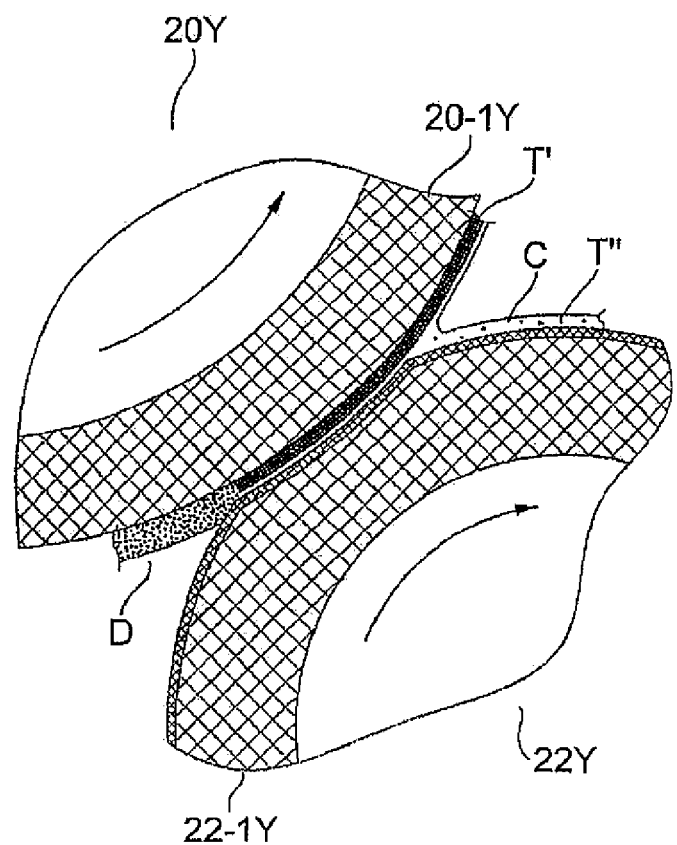
FIG. 4 is a diagram showing compression of developer performed by a developer compressing roller according to an embodiment of the invention.
Figure 5:
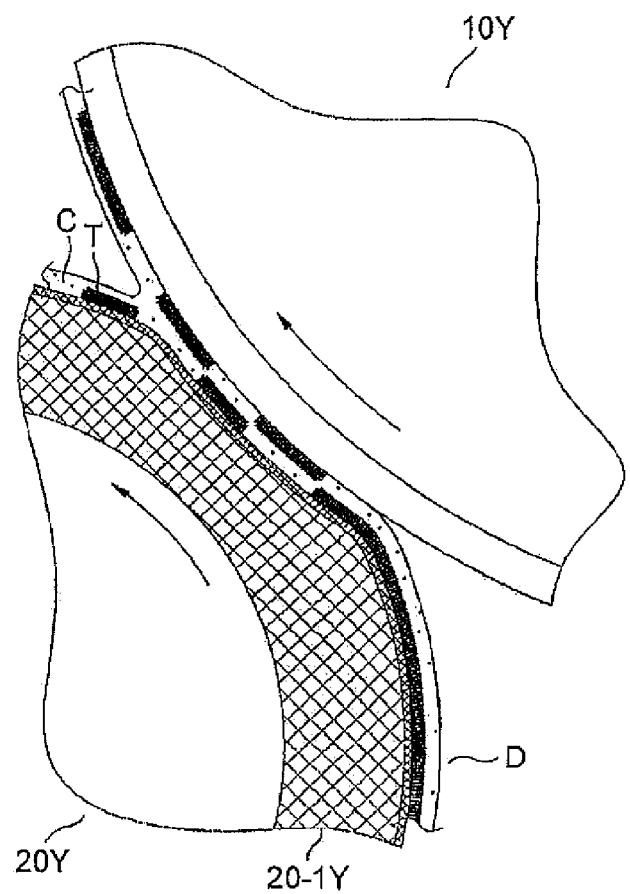
FIG. 5 is a diagram showing a developing process performed by a developing roller according to an embodiment of the invention.
Figure 6:
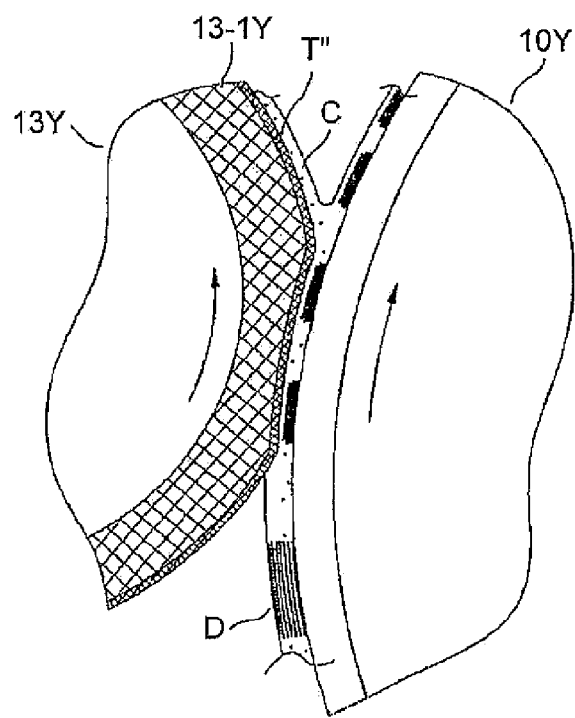
FIG. 6 is a diagram showing a squeezing operation performed by an image carrier squeezing roller according to an embodiment of the invention.

The image forming units and the developing units are now described. FIG. 2 is a cross-sectional view of major constituent elements of an image forming unit and a developing unit. FIG. 3 is a diagram showing a developer supplying member. FIG. 4 is a diagram showing compression of the developer performed by the developer compressing roller 22Y. FIG. 5 is a diagram showing a developing process performed by the developing roller 20Y. FIG. 6 is a diagram showing a squeezing operation performed by an image carrier squeezing roller 13Y. Since the configurations of the image forming units and the developing units for each color are the same, only an image forming unit and a developing unit of yellow color Y are described hereinafter.

In the image forming unit, a neutralization device 16Y, a cleaning device including an image carrier cleaning blade 17Y and a developer collecting unit 18Y, a corona charging 11Y, an exposure unit 12Y, a developing roller 20Y of the developing unit 30Y, and a squeeze device including an image carrier squeezing roller 13Y and an image carrier squeezing roller cleaning blade 14Y are disposed along the rotation direction of the outer periphery of the image carrier 10Y. In addition, a cleaning blade 21Y and a developer supplying roller 32Y using an anilox roller are disposed on the outer periphery of the developing roller 20Y of the developing unit 30Y. A liquid developer agitating paddle 36Y and a developer supplying roller 32Y are housed inside the liquid developer container 31Y. In addition, a primary transfer roller 51Y of the primary transfer unit is disposed along the intermediate transfer body 40 in a position facing the image carrier 10Y.

The image carrier 10Y is a photosensitive drum that has a width larger than that of the developer roller 20Y of about 320 mm and comprises a cylindrical member having a photosensitive layer formed on its outer peripheral surface. As shown in FIG. 2, the image carrier 10Y is rotated in the clockwise direction. The photosensitive layer of the image carrier 10Y is formed of an organic image carrier, an amorphous silicon image carrier, or the like. The corona charging 11Y is disposed on the upstream side of a nip part of the image carrier 10Y and the developing roller 20Y in the rotation direction of the image carrier 10Y. A bias having the same polarity as the charging polarity of developing toner particles is applied by a power supply device to the corona charging 11Y, to charge the image carrier 10Y. The exposure unit 12Y, on the downstream side of the corona charging 11Y in the rotation direction of the image carrier 10Y, forms an electrostatic latent image on the image carrier 10Y by exposing the upper surface of the image carrier 10Y that is charged by the corona charging 11Y.

The developing unit 30Y includes the developer container 31Y that stores liquid developer in a state that toner having a weight ratio of about 25% is dispersed into carrier liquid; the developing roller 20Y that carries the liquid developer; the developer supplying roller 32Y; a regulating blade 33Y; the agitating paddle 36Y that is used for agitating the liquid developer to maintain the liquid developer in a constant dispersion state, and for supplying the liquid developer to the developing roller 20Y; a supply unit 35Y that supplies the liquid developer to the agitating paddle 36Y from a liquid developer storing unit 71Y; the developing roller cleaning blade 21Y that performs a cleaning operation for the developing roller 20Y; and a collecting screw 34Y that collects and sends the liquid developer scraped by the developing roller cleaning blade 21Y and the image carrier squeezing roller cleaning blade 14Y to the liquid developer storing unit 71Y.

The liquid developer housed in the developer container 31Y is not a generally-used volatile liquid developer having low density (about 1-2 wt %), low viscosity, and volatile at room temperature and using Isopar (trademark of Exxon) as a carrier liquid, but instead is a non-volatile liquid developer having high density, high viscosity, and non-volatile at room temperature. In other words, the liquid developer according to an embodiment of the invention is a high-viscosity (about 30-10000 mPa·s) liquid developer that is prepared by adding solids having an average diameter of 1 μm, in which colorants such as pigments are dispersed in a thermoplastic resin, into a liquid solvent such as an organic solvent, silicon oil, mineral oil, or cooking oil with a dispersant to have a toner solid content of about 25%.

The developer supplying roller 32Y, as shown in FIG. 3, is a cylindrical member and is an anilox roller having a corrugated surface in which delicate spiral grooves are uniformly formed so as to easily carry the developer on the surface. The developer supplying roller 32Y may be rotated, for example, in the clockwise direction as shown in FIG. 2. In regard to the size of the grooves, the pitch of the grooves is about 130 μm, and the depth of the grooves is about 30 μm. The liquid developer is supplied from the developer container 31Y to the developing roller 20Y by the developer supplying roller 32Y. The agitating paddle 36Y and the developer supplying roller 32Y may be brought into contact with each other in a slidable manner or may be separated from each other.

The regulating blade 33Y is configured by an elastic blade formed by coating the surface with an elastic body, such as a rubber part formed of urethane rubber or the like, that is brought into contact with the surface of the developer supplying roller 32Y, and a plate formed of metal or the like that supports the rubber part. The regulating blade 33Y controls the amount of the liquid developer supplied to the developing roller 20Y by regulating and controlling the film thickness and amount of the liquid developer that is carried and transported in the developer supplying roller 32Y. The rotation direction of the developer supplying roller 32Y may not be a direction denoted by an arrow shown in FIG. 2 and may instead be a direction opposite thereto. In such a case, the regulating blade 33Y is disposed in correspondence with the rotation direction.

The developing roller 20Y is a cylindrical member having a width of about 320 mm and is rotated about a rotating shaft in the counterclockwise direction as shown in FIG. 2. The developing roller 20Y is configured by forming an elastic layer formed of polyurethane rubber, silicon rubber, NBR, or the like on an outer periphery of an inner core formed of metal such as iron. The developing roller cleaning blade 21Y is formed of rubber or the like that is brought into contact with the surface of the developing roller 20Y. The developing roller 20Y is disposed on the downstream side of a developing nip part that is brought into contact with the image carrier 10Y in the rotation direction of the developing roller 20Y, and the developing roller cleaning blade 21Y scrapes and removes liquid developer remaining in the developing roller 20Y.

The developer compressing roller 22Y is a cylindrical member and, similar to the developing roller 20Y, is in the form of an elastic roller configured by coating an elastic body 22-1Y (FIG. 4). The developer compressing roller 22Y has a structure in which a conductive resin layer or a rubber layer is formed on a surface layer of a metal roller base material. As shown in FIG. 2, the developer compressing roller 22Y may be rotated in the clockwise direction that is opposite to the rotation direction of the developing roller 20Y. The developer compressing roller 22Y has a unit for increasing the charging bias of the surface of the developing roller 20Y. The developer that has been transported by the developing roller 20Y, as shown in FIGS. 2 and 4, applies an electric field from the developer compressing roller 22Y side to the developing roller 20Y in a developer compressing part in which the developer compressing roller 22Y is sled to be brought into contact with the developing roller 20Y to form a nip. The unit for applying the electric field for compressing the developer may be, for example, a corona discharger that generates corona discharge, instead of the roller shown in FIG. 2.

As shown in FIG. 4, toner T uniformly dispersed into the carrier liquid C is moved by the developer compressing roller 22Y to be aggregated to the developing roller 20Y side, and a so-called developer compressing state T' is formed. In addition, a part of the carrier liquid C and a small amount of toner T" that is not in the developer compressing state are carried and rotated in a direction denoted by the arrow shown in FIG. 4 by the developer compressing roller 22Y, and are scraped to be removed by the developer compressing roller cleaning blade 23Y, and are merged with the developer inside the reservoir 31Y to be reused. On the other hand, the developer D that is carried in the developing roller 20Y to be developer-compressed is, as shown in FIG. 5, in a developing nip part in which the developing roller 20Y is brought into contact with the image carrier 10Y, developed in correspondence with the latent image of the image carrier 10Y by application of a required electric field. The remaining developer D after development is then scraped to be removed by the developing roller cleaning blade 21Y and is merged with the developer inside the reservoir 31Y to be reused. The merged carrier liquid and toner are not in a state of a mixed color.

The image carrier squeeze device is disposed on the downstream side of the developing roller 20Y to face the image carrier 10Y and collects remaining developer in the image carrier 10Y after development of a toner image. As shown in FIG. 2, the image carrier squeeze device includes the image carrier squeezing roller 13Y formed of an elastic roller member that has the surface coated with an elastic body 13a*y* and is sled to be brought into contact with the image carrier 10Y for being rotated and the cleaning blade 14Y that is sled to be brought into contact with the image carrier squeezing roller 13Y in a pressing manner so as to clean the surface.

The primary transfer unit 50Y transfers a developer image developed on the image carrier 10Y on the intermediate transfer body 40 by using the primary transfer roller 51Y. Here, a configuration in which the image carrier 10Y and the intermediate transfer body 40 are moved at a constant speed is used. Accordingly, the driving load for rotation and movement is reduced, and disturbance of the developed toner image due to the image carrier 10Y is suppressed.

The developer collecting and supplying device 70Y has the liquid developer storing unit 71Y that stores the collected liquid developer and controls density of the liquid developer by supplying high-density developer from a developer tank 74Y and a carrier liquid from a carrier liquid tank 77Y.

In this embodiment, the liquid developer is collected from the developing unit 30Y and the image carrier 10Y. The liquid developer collected by the developer collecting screw 34Y of the developing unit 30Y is collected into the liquid developer storing unit 71Y through a developing unit collecting path 72Y. In addition, the liquid developer collected by the cleaning device that is configured by the image carrier cleaning blade 17Y and the developer collecting unit 18Y from the image carrier 10Y is collected into the liquid developer storing unit 71Y through an image carrier collecting path 73Y.

The high-density developer is supplied from the developer tank 74Y to the liquid developer storing unit 71Y through a developer supplying path 75 and a developer pump 76. The carrier liquid is supplied from the carrier liquid tank 77Y to the liquid developer storing unit 71Y through a carrier liquid supplying path 78Y and a carrier liquid pump 79Y. Instead of a pump, a structure in which the developer or the carrier liquid is supplied by opening or closing a valve or the like using gravity may be used.

The liquid developer stored in the liquid developer storing unit 71Y is supplied to the developer container 31Y through a developer supplying path 81Y and a developer supplying pump 82Y.

Operation of the image forming apparatus according to an embodiment of the invention is now described. The image forming unit of yellow color and the developing unit 30Y from among the four image forming and developing units will be described as examples.

In the developer container 31Y, toner particles inside the liquid developer have positive charges. The liquid developer is pumped from the developer container 31Y by agitating the liquid developer by using the agitating paddle 36Y to rotate the developer supplying roller 32Y.

The regulating blade 33Y is brought into contact with the surface of the developer supplying roller 32Y, leaves liquid developer inside the anilox-patterned grooves that are formed on the corrugated surface of the developer supplying roller 32Y, and scrapes other remaining liquid developer. Accordingly, the regulating blade 33Y regulates the amount of liquid developer to be supplied to the developing roller 20Y. By the above-described regulating operation, the film thickness of liquid developer coated on the developing roller 20Y is quantified to be about 6 μm. Then, the liquid developer scraped by the regulating blade 33Y is fallen to be returned to the developer container 31Y by gravity. On the other hand, liquid developer that has not been scraped by the regulating blade 33Y is stored in the grooves of corrugated surface of the developer supplying roller 32Y and is pressed by the developing roller 20Y, and accordingly, the liquid developer is coated on the surface of the developing roller 20Y.

The developing roller 20Y on which the liquid developer is coated by the developer supplying roller 32Y is brought into contact with the developer compressing roller 22Y on the downstream of a nip part between the developer supplying roller 32Y and the developing roller 20Y. A bias of about +400 V is applied to the developing roller 20Y. In addition, a bias that is higher than that of the developing roller 20Y and has a same polarity as the charging polarity of the toner is applied to the developer compressing roller 22Y. For example, a bias of about +600 V may be applied to the developer compressing roller 22Y. Accordingly, toner particles inside the liquid developer on the developing roller 20Y, as shown in FIG. 4, are moved to the developing roller 20Y side at the moment when the toner particles pass the nip between the developer compressing roller 22Y and the developing roller 20Y. Accordingly, a state that the toner particles are gently combined together and formed as a film is formed. Thus, in a developing process at the image carrier 20Y, the toner particles are moved from the developing roller 20Y to the image carrier 10Y in a prompt manner, and the image density is thereby improved.

The image carrier 10Y is formed of amorphous silicon. After the surface of the image carrier 10Y is charged at about +600 V by the corona charging 11Y on the upstream of a nip part between the developing roller 20Y and the image carrier 10Y, a latent image is formed on the image carrier 10Y, so that the electric potential of the image part is set to +25 V by the exposure unit 12Y. In the developing nip part formed between the developing roller 20Y and the image carrier 10Y, as shown in FIG. 5, the toner particles T are selectively moved to the image part on the image carrier 10Y in accordance with an electric field formed by the bias of +400 V applied to the developing roller 20Y and the latent image (image part +25 V, non-image part +600 V) on the image carrier 10Y, and thereby a toner image is formed on the image carrier 10Y. In addition, since the carrier liquid C is not influenced by the electric field, as shown in FIG. 5, the carrier liquid is divided at the outlet of the developing nip part of the developing roller 20Y and the image carrier 10Y, and thus, the carrier liquid is adhered to both the developing roller 20Y and the image carrier 10Y.

The image carrier 10Y passing through the developing nip part passes through the image carrier squeezing roller 13Y part. The image carrier squeezing roller 13Y, as shown in FIG. 6, has a function for increasing the toner particle ratio of a developed image by collecting the remaining carrier liquid C from the developer D developed on the image carrier 10Y and originally unnecessary redundant toner T". The capability of collecting the remaining carrier liquid C can be set to a required level by using the rotation direction of the image carrier squeezing roller 13Y and a relative difference of the circumferential velocity of the surface of the image carrier squeezing roller 13Y with respect to the circumferential velocity of the surface of the image carrier 10Y. When the image carrier squeezing roller 13Y is rotated in a counter direction with respect to the image carrier 10Y, the collection capability increases. In addition, as the above-described difference between the circumferential velocities is set to be large, the collection capability increases, and thus, an additional synergetic effect can be acquired.

In this embodiment, as an example, the image carrier squeezing roller 13Y is rotated at approximately the same circumferential velocity as that of the image carrier 10Y as shown in FIG. 6 and a redundant carrier liquid C having a weight ratio of about 5 to 10% is collected from the developer D developed on the image carrier 10Y. Accordingly, both loads for driving rotation are reduced, and disturbance of the developed toner image due to the image carrier 10Y is suppressed. The redundant carrier liquid C and the unnecessary redundant toner T" that have been collected by the image carrier squeezing roller 13Y are collected from the image carrier squeezing roller 13Y into the developer container 31Y by the operation of the cleaning blade 14Y. In addition, since the redundant carrier liquid C and the redundant toner T" collected as described above are collected from an isolated dedicated image carrier 10Y, a phenomenon of color mixture does not occur in all the spots.

Next, the image carrier 10Y passes the nip part between the intermediate transfer body 40 and the image carrier 10Y, so that the primary transfer of the developed toner image onto the intermediate transfer body 40 is performed by the primary transfer unit 50Y. About −200 V having a polarity opposite to that of the charged polarity of the toner particles is applied to the primary transfer roller 51Y, and accordingly the toner is primary transferred onto the intermediate transfer body 40 from the image carrier 10Y, and only the carrier liquid remains in the image carrier 10Y. On the downstream side of the primary transfer unit in the rotation direction of the image carrier 10Y, the electrostatic latent image is eliminated from the image carrier 10Y after the primary transfer by the neutralization device 16Y formed of LEDs or the like. Then, the remaining carrier liquid on the image carrier 10Y is scraped off by the image carrier cleaning blade 17Y and is collected to the developer collecting unit 18Y.

The toner image formed on the intermediate transfer body 40 that is carried in a superposing manner by primary transforming toner images formed on a plurality of image carriers 10 one after another advances to the secondary transfer unit 60 and enters into the nip part between the intermediate transfer body 40 and the secondary transfer roller 61. The width of the nip part is set to 3 mm. In the secondary transfer unit 60, −1200 V is applied to the secondary roller 61, and +200 V is applied to the belt driving roller 41. Accordingly, the toner image on the intermediate transfer body 40 is transferred onto a recording medium (sheet member) such as a paper sheet.

However, when a trouble in supplying the sheet member such as a jam occurs, not all the toner images are transferred onto the secondary transfer roll to be collected, and a part of the toner images remains on the intermediate transfer body. In addition, in an ordinary secondary transfer process, not 100% of the toner image formed on the intermediate transfer body is secondary transferred to be transited onto the sheet member, and several percentages of secondary transfer remain. In particular, when a trouble in supplying the sheet member such as a jam occurs, the toner image is brought into contact with the secondary transfer roller 61 to be transferred in a state that the sheet member is not interposed therebetween, and thus the rear surface of the sheet member gets dirty. In a process for not transferring the unnecessary toner images, in this embodiment, a bias that is in the direction for pressing the toner particles of the liquid developer to the intermediate transfer body and has a same polarity as the charged polarity of the toner particles is applied to the secondary transfer roller 61 in a non-transfer process. Accordingly, the toner particles of the liquid developer remaining on the intermediate transfer body 40 is pressed to the intermediate transfer body 40 side to be in a compaction state, and the carrier liquid is collected (squeezed) at the secondary transfer roller 61 side. Then a cleaning operation for the surface of the intermediate transfer body 40 is performed by using the intermediate transfer body cleaning blade 46, and a cleaning operation for the surface of the secondary transfer roller 61 is performed by using the secondary roller cleaning blade 62 is performed.

The cleaning device of the intermediate transfer body 40 is now described. When a trouble in supplying the sheet member such as a jam occurs, not all the toner images are transferred onto the secondary transfer roller 61 to be collected, and thus, a part of the toner images remains on the intermediate transfer body 40. In addition, in an ordinary secondary transfer process, not 100% of the toner image formed on the intermediate transfer body 40 is secondary transferred to be transited onto the sheet member, and several percent of secondary transfer remains. These two types of unnecessary toner images are collected by the intermediate transfer body cleaning blade 46 and the developer collecting unit 47 that are disposed to be brought into contact with the intermediate transfer body 40 for forming the next image. In such a non-transfer process, a bias for pressing the remaining toner on the intermediate transfer body 40 to the intermediate transfer body 40 is applied to the secondary transfer roller 61.

A density measuring device 120Y is now described. As shown in FIG. 2, the density measuring device 120Y has an agitating propeller shaft 121Y, a transparent propeller 122Y as an example of a moving member, an agitating propeller 123Y as an example of an agitating member, a motor 124Y, and a density measuring unit 130Y.

The transparent propeller 122Y and the agitating propeller 123Y are disposed on a same shaft: the agitating propeller shaft 121Y. The agitating propeller shaft 121Y is a member that is rotated by the motor 124Y.

Figure 7:
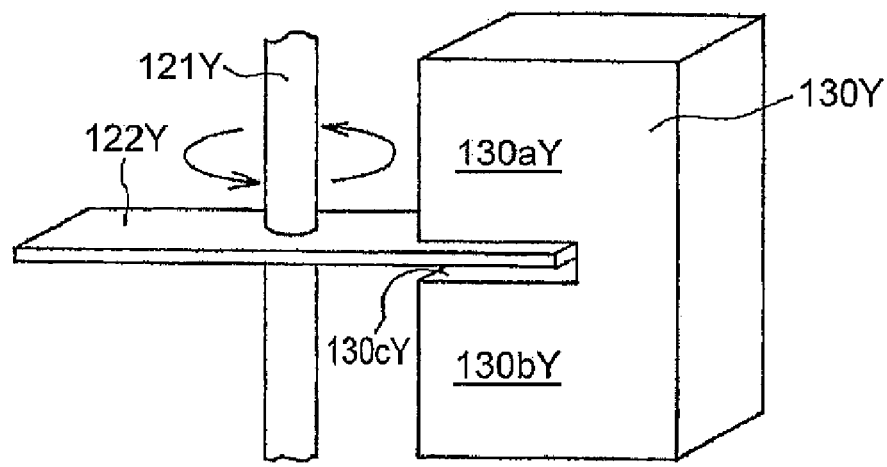
FIG. 7 is an enlarged view of a part in the vicinity of a transparent propeller shown in FIG. 2.
Figures 8A, 8B:
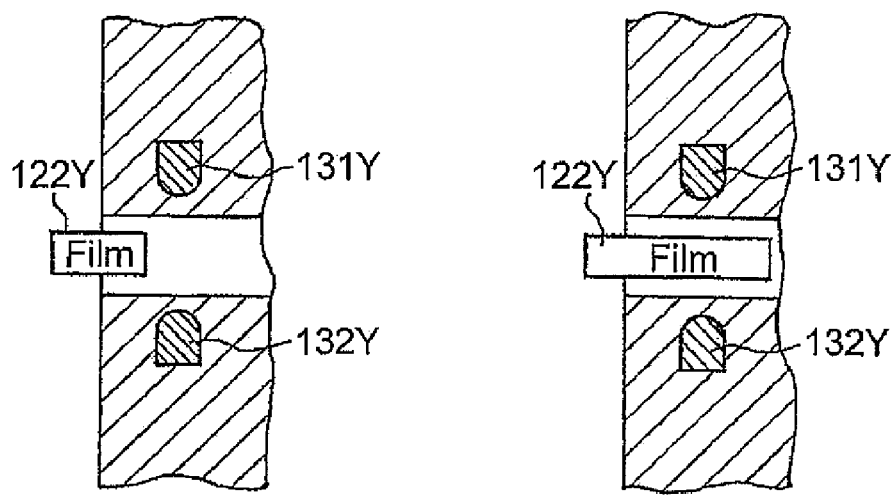
FIGS. 8A and 8B are enlarged views of a gap.
Figure 9:
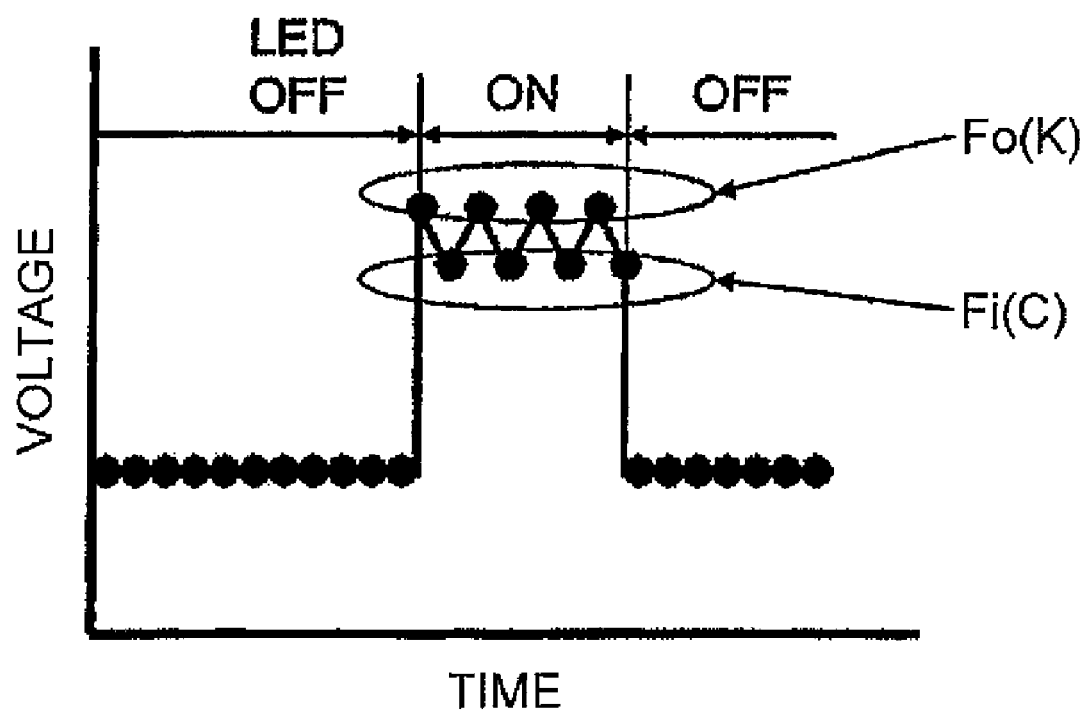
FIG. 9 is a diagram showing a change of a signal output from a density-measuring light receiving element according to an embodiment of the invention.
Figure 10A:
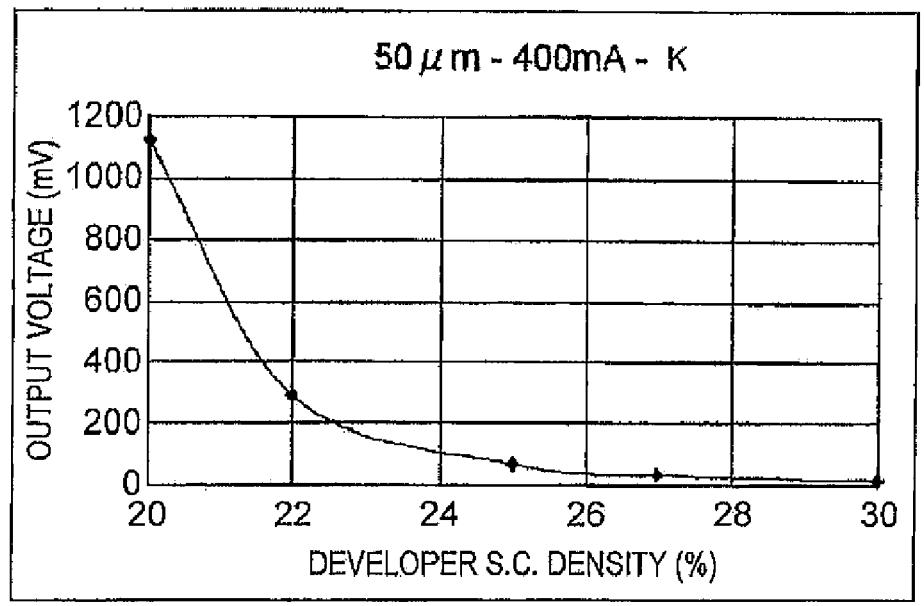
FIGS. 10A and 10B are graphs showing a relationship between output voltage of the density-measuring light receiving element and the density of liquid developer according to an embodiment of the invention.
Figure 10B:
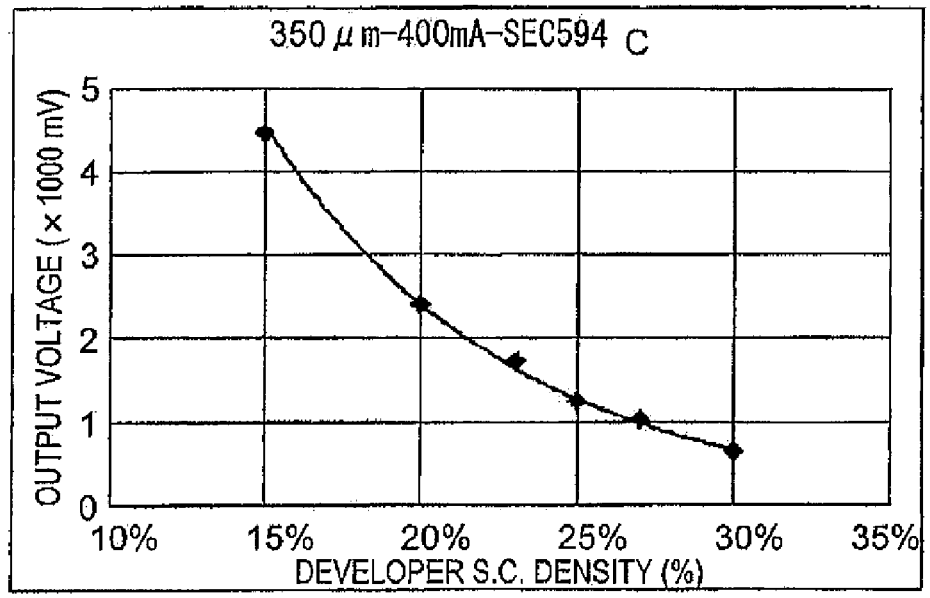
Figure 11:
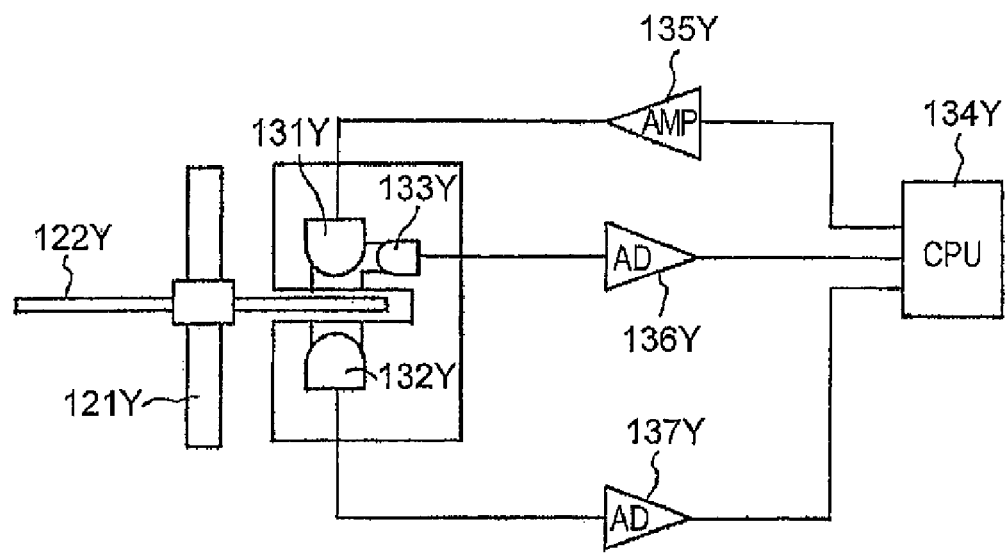
FIG. 11 is a system diagram of a transmission-type density measuring unit according to an embodiment of the invention.
Figure 12:
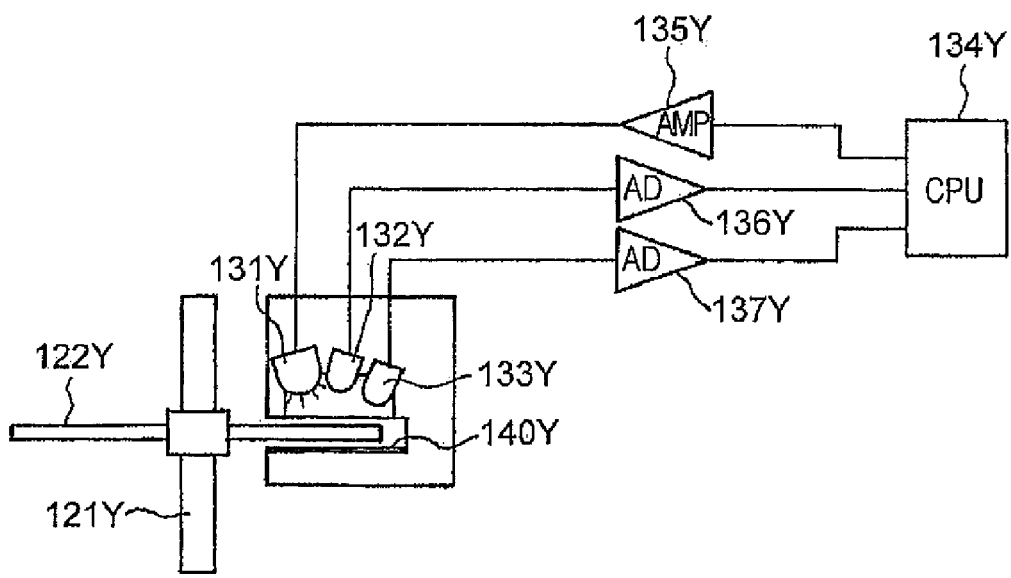
FIG. 12 is a system diagram of a reflection-type density measuring unit according to an embodiment of the invention.

A density detecting method using the density measuring unit 130Y and the transparent propeller 122Y is now described. FIG. 7 is an enlarged view of a part in the vicinity of the transparent propeller 122Y shown in FIG. 2. FIGS. 8A and 8B are enlarged views of a gap. FIG. 9 is a diagram showing a change of a signal output from a density-measuring light receiving element 132Y. FIGS. 10A and 10B are graphs showing a relationship between the output voltage of the density-measuring light receiving element 132Y and the density of liquid developer. FIG. 11 is a system diagram of a transmission-type density measuring unit 130Y. FIG. 12 is a system diagram of a reflection-type density measuring unit 130Y.

As shown in FIG. 7, the transparent propeller 122Y is supported by the agitating propeller shaft 121Y and is formed of a member having a flat plate shape such as a rectangle that can be rotatable. The transparent propeller 122Y has a structure for intermittently passing a gap 130cY between first and second members 130aY and 130bY of the density measuring unit 130Y. The first member 130aY or the second member 130bY can be moved, and thus a distance of the gap 130cY can be changed. The distance of the gap 130cY may be changed in accordance with the color of the liquid developer.

Next, a simple principle of the density detecting method is described. FIGS. 8A and 8B are enlarged views of the gap. FIG. 9 is a diagram showing a change of a signal output from the density-measuring light receiving element 132Y. As shown in FIG. 8A, when the transparent propeller 122Y is not positioned between a light emitting diode (LED) 131Y and the density-measuring light receiving element 132Y, the density-measuring light receiving element 132Y outputs a signal having a smaller value Fo in the graph shown in FIG. 9. As shown in FIG. 8B, when the transparent propeller 122Y is positioned between the light emitting diode (LED) 131Y and the density-measuring light receiving element 132Y, the density-measuring light receiving element 132Y outputs a signal having a larger value Fi in the graph shown in FIG. 9. In this embodiment, a value for acquiring a density value is selected for each color. For example, for black, a density value is acquired by averaging values Fi, and for cyan, a density value is acquired by averaging values Fo.

FIGS. 10A and 10B are graphs showing a relationship between the output voltage of the density-measuring light receiving element 132Y and the density of liquid developer. FIG. 10A shows a relationship between the output voltage of the density-measuring light receiving element 132Y and the density of liquid developer for black. In addition, FIG. 10B shows a relationship between the output voltage of the density-measuring light receiving element 132Y and the density of liquid developer for cyan.

In the transmission-type density measuring unit 130Y as shown in FIG. 11, a light emitting diode (LED) 131Y as an example of the density measuring member and the density-measuring light receiving element 132Y are disposed to face each other with a gap 130cY interposed therebetween. On the light emitting diode (LED) 131Y side, an emission intensity-measuring light receiving element 133Y as a second light receiving element is disposed.

Light emitted from the light emitting diode (LED) 131Y has a light path formed though liquid developer on the light emitting diode (LED) 131Y side relative to the transparent propeller 122Y, the transparent propeller 122Y, and liquid developer on the density-measuring light receiving element 132Y side relative to the transparent propeller 122Y to the density-measuring light receiving element 132Y, and a light path formed through the liquid developer on the light emitting diode (LED) 131Y side relative to the transparent propeller 122Y to the emission intensity-measuring light receiving element 133Y.

The light emitting diode (LED) 131Y, the density-measuring light receiving element 132Y and the emission intensity-measuring light receiving element 133Y are connected to a CPU 134Y. The light emitting diode (LED) 131Y is connected to the CPU 134Y through an amplifier 135Y. The density-measuring light receiving element 132Y is connected to the CPU 134Y through a first A/D converter 136Y. The emission intensity-measuring light receiving element 133Y is connected to the CPU 134Y through a second A/D converter 137.

In the reflection-type density measuring unit 130Y as shown in FIG. 12, the light emitting diode (LED) 131Y, the density-measuring light receiving element 132Y, and the emission intensity-measuring light receiving element 133Y are disposed on one side of a gap 130cY. A reflective film 140Y is disposed on the other side of the gap 130cY.

Under such a structure, light emitted from the light emitting diode (LED) 131Y has a light path formed though liquid developer on the light emitting diode (LED) 131Y side relative to the transparent propeller 122Y, the transparent propeller 122Y, and liquid developer on the reflective film 140Y side, reflected from the reflective film 140Y, and then through liquid developer on the reflective film 140Y side, the transparent propeller 122Y, liquid developer on the density-measuring light receiving element 132Y side relative to the transparent propeller 122Y to the density-measuring light receiving element 132Y and a light path formed through the liquid developer on the light emitting diode (LED) 131Y side relative to the transparent propeller 122Y to the emission intensity-measuring light receiving element 133Y.

The light emitting diode (LED) 131Y, the density-measuring light receiving element 132Y and the emission intensity-measuring light receiving element 133Y are connected to the CPU 134Y. The light emitting diode (LED) 131Y is connected to the CPU 134Y through an amplifier 135Y. In addition, the density-measuring light receiving element 132Y is connected to the CPU 134Y through a first A/D converter 131Y. The emission intensity-measuring light receiving element 133Y is connected to the CPU 134Y through a second A/D converter 137Y.

Figure 13:
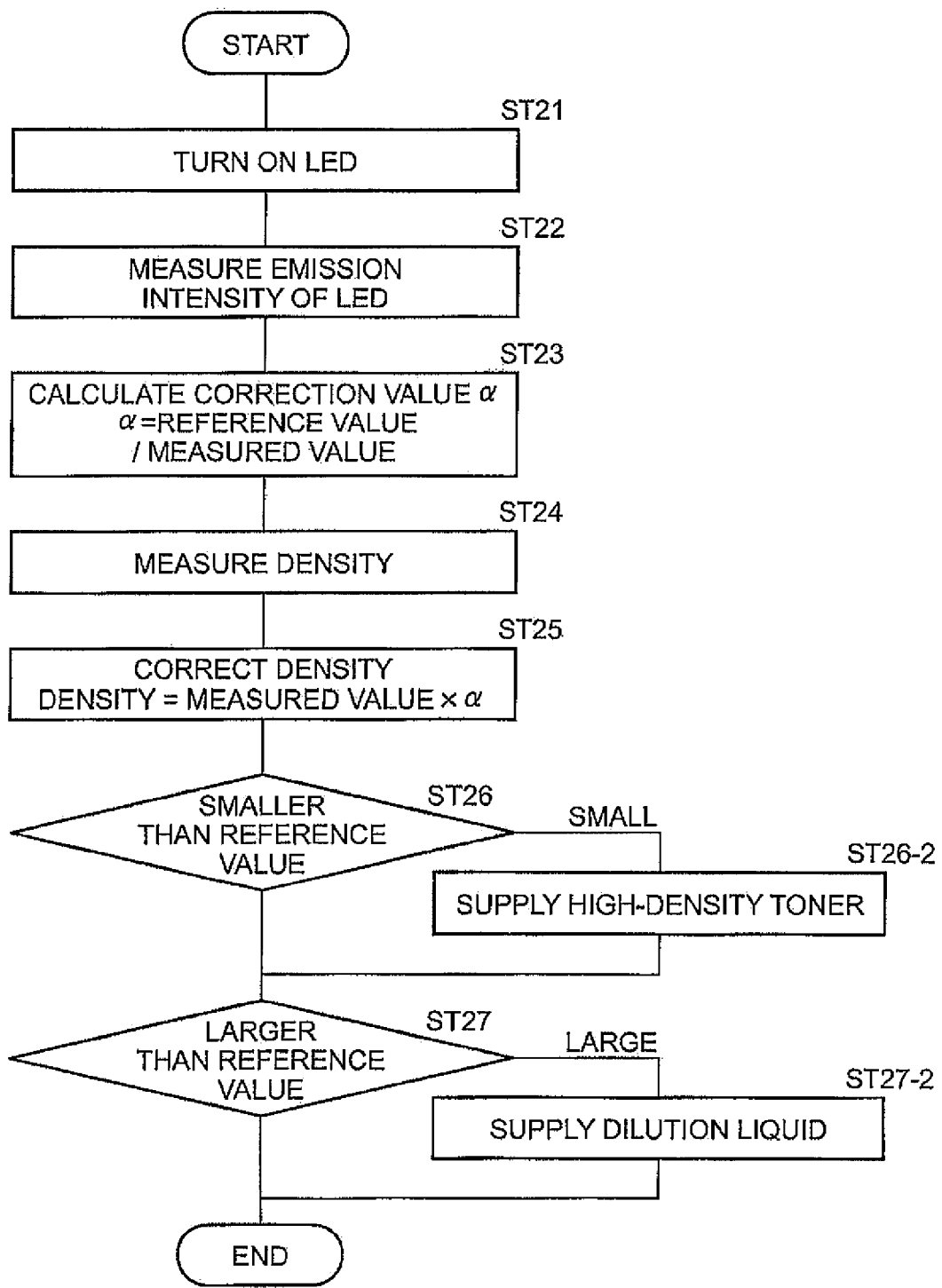
FIG. 13 is a flowchart of a detection process of a density detecting unit according to an embodiment of the invention.

A detection method using the density measuring device 120Y is now described. FIG. 13 is a flowchart of a detection process of the density measuring device 120Y.

First, in Step 21, the light emitting diode (LED) 131Y is turned on (ST21). Subsequently, in Step 22, the light intensity of the light emitting diode (LED) 131Y is measured by using the emission intensity-measuring light receiving element 133Y (ST22).

Next, in Step 23, a correction value a is calculated (ST23). The correction value a is acquired by comparing a measured value measured by the emission intensity-measuring light receiving element 133Y with a reference value of the light emitting diode (LED) 131Y stored in advance.

Next, in Step 24, the density is measured by using the density-measuring light receiving element 132Y (ST24).

In Step 25, the density of the liquid developer is acquired by performing density correction by using the CPU 134Y (ST25). The density of the liquid developer is acquired by multiplying the measured value that has been measured by the density-measuring light receiving element 132Y in Step 24 by the correction value α acquired in Step 23.

Next, in Step 26, it is determined whether the density of the liquid developer is smaller than a density reference value stored in advance (ST26). When the density of the liquid developer is determined to be smaller than the density reference value, in Step 26-2, high-density developer is supplied from the developer tank 74Y to the liquid developer storing unit 71Y through a developer supplying path 75Y and a developer pump 76Y (ST26-2).

On the other hand, when the density of the liquid developer is determined not to be smaller than the density reference value in Step 26, it is determined whether the density of the liquid developer is larger than the density reference value stored in advance in Step 27 (ST27). When the density of the liquid developer is determined to be larger than the density reference value, in Step 27-2, the carrier liquid is supplied from the carrier liquid tank 77Y to the liquid developer storing unit 71Y though the carrier liquid supplying path 78Y and the carrier liquid pump 79Y (ST27-2).

By controlling the density of the liquid developer as described above, the density of the liquid developer inside the liquid developer storing unit 71Y becomes approximately constant.

Figure 14:
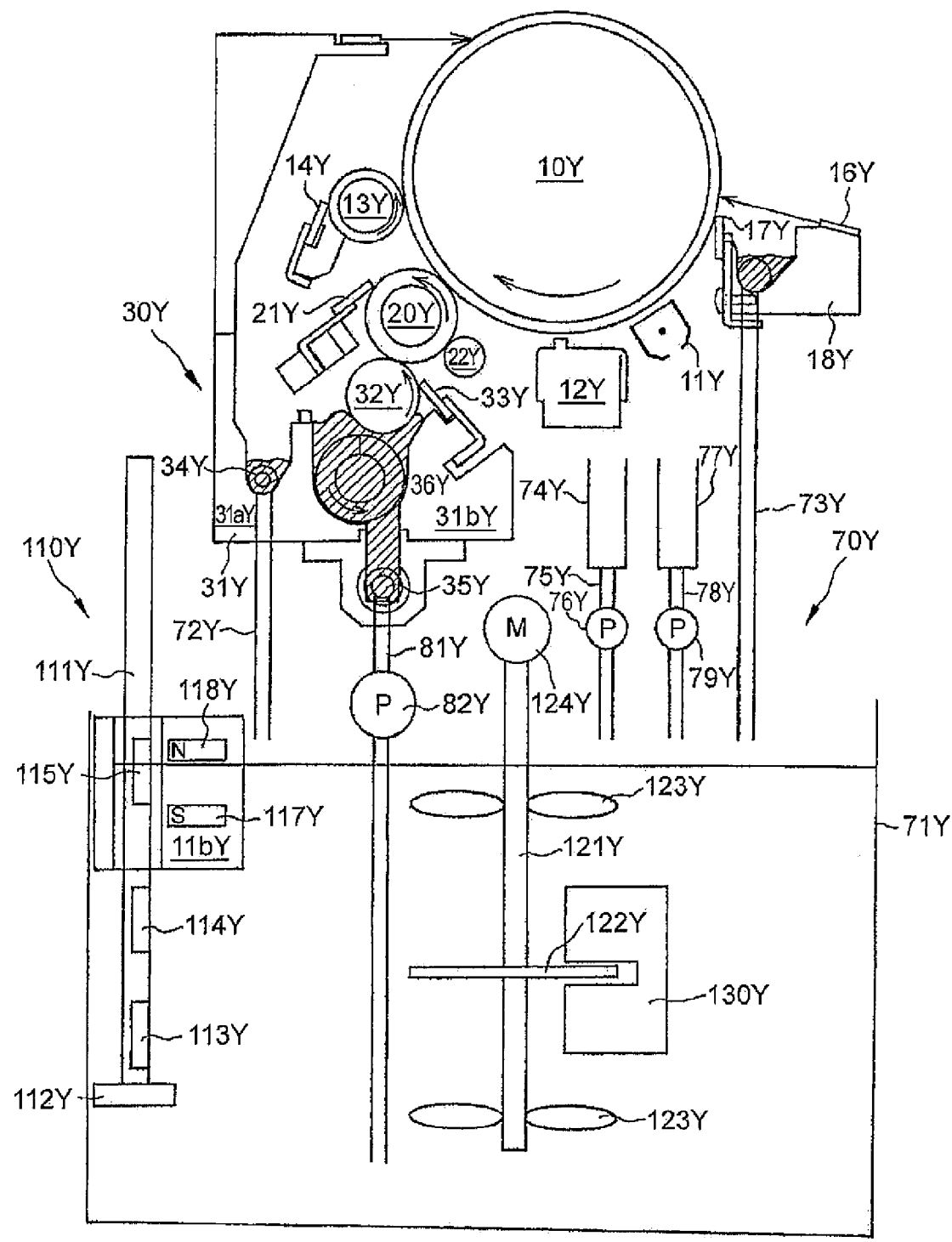
FIG. 14 is a diagram of a liquid-level detecting unit and a density detecting unit according to an embodiment of the invention.

As another embodiment of the invention, a liquid-level detecting unit 110Y as shown in FIG. 14 may be provided.

The liquid-level detecting unit 110Y is now described. As shown in FIG. 14, the liquid-level detecting unit 110Y has a float supporting member 111Y, a regulating member 112Y, a first hole element 113Y, a second hole element 114Y, a third hole element 115Y, a float 116Y as an example of a floating member, and first and second magnetic field generators 117Y and 118Y.

The float supporting member 111Y is formed of a member that supports the float 116Y to be movable from a position on the liquid surface inside the liquid developer storing unit 71Y to an approximate bottom part below the liquid surface. On the upper side of the float supporting member 111Y, an upper regulating member 112aY is disposed, and a lower regulating member 112bY is disposed on the lower side of the float supporting member. In addition, between the lower regulating member and the upper regulating member, the first hole element 113Y, the second hole element 114Y, and the third hole element 115Y are sequentially disposed from the bottom with a predetermined distance apart therebetween.

The first hole element 113Y, the second hole element 114Y, and the third hole element 115Y are formed of proportional output-type hole members of which output voltage changes in accordance with magnetic flux density. In this embodiment, the distance between the hole elements is set to 30 mm.

The float 116Y is a member that is movable relative to the float supporting member 111Y by floating on the liquid surface in accordance with the position of the liquid surface. On the lower side of the float 116Y, the first magnetic field generator 117Y is disposed, and the second magnetic field generator 118Y is disposed on the upper side thereof to be a predetermined distance apart from the first magnetic field generator 117Y.

The first magnetic field generator 117Y and the second magnetic field generator 118Y are disposed to be moved in accordance with movement of the float 116Y with facing the hole elements 113Y, 114Y, and 115Y. The first magnetic field generator 117Y and the second magnetic field generator 118Y are disposed to have the north (N) pole and the south (S) pole disposed on opposite sides to each other. In this embodiment, the magnetic field generators 117Y and 118Y have a diameter of 5 mm, a length of 6 mm, and 4000 Gauss, and are spaced apart by 20 mm.

A method of converting outputs of the hole elements 113Y, 114Y, and 115Y into distances when the liquid-level detecting unit 110Y is operated is now described.

Figure 15:
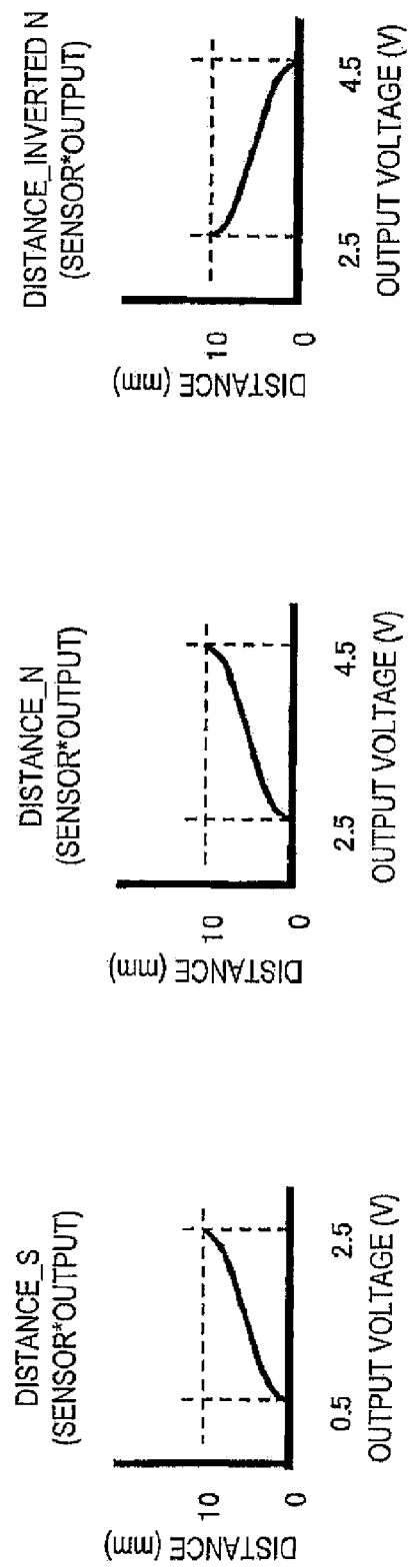
FIGS. 15A, 15B, and 15C are diagrams showing tables used for converting outputs of hole elements into distances according to an embodiment of the invention.

FIGS. 15A, 15B, and 15C are diagrams showing tables used for converting outputs of the hole elements 113Y, 114Y, and 115Y into distances. FIG. 15A is a first table showing a relationship between the output voltage of each hole element and a distance in a case where the south (S) pole is detected. FIG. 15B is a second table showing a relationship between the output voltage of each hole element and a distance in a case where the north (N) pole is detected. FIG. 15C is a third table showing a relationship between the output voltage of each hole element and a distance in a case where the inverted-north (N) pole is detected.

Figure 16:
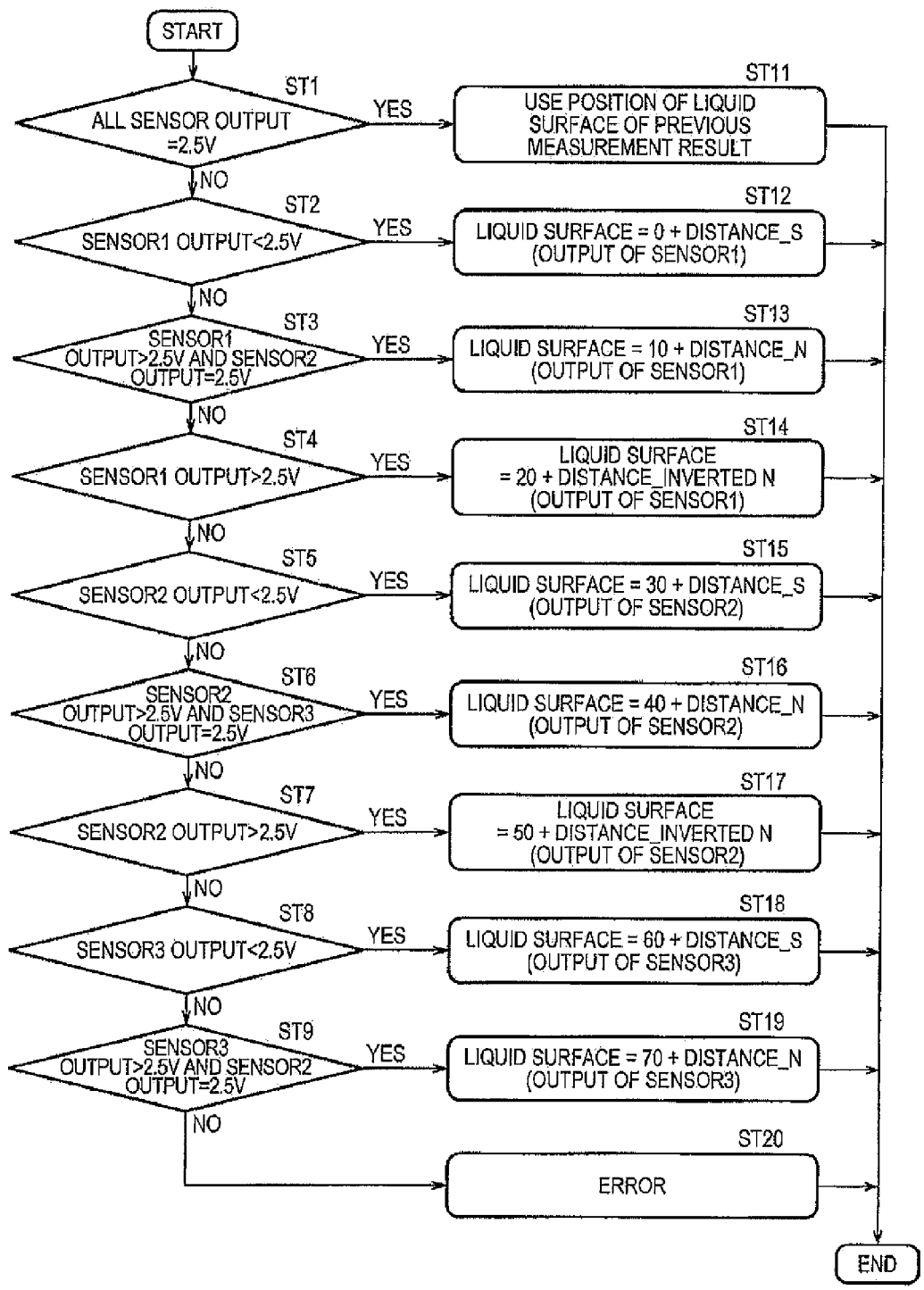
FIG. 16 is a flowchart of a process for converting the outputs of the hole elements into distances according to an embodiment of the invention.

FIG. 16 is a flowchart of a process for converting the outputs of the hole elements 113Y, 114Y, and 115Y into distances.

First, in Step 1, it is determined whether outputs of all the hole elements 113Y, 114Y, and 115Y are 2.5 V (ST1).

When the outputs of all the hole elements 113Y, 114Y, and 115Y are 2.5 V in Step 1, the result of the previous measurement is used as the position of the liquid surface in Step 11 (ST11), and the process ends. On the other hand, when the outputs of all the hole elements 113Y, 114Y, and 115Y are not 2.5 V in Step 1, it is determined whether the output of the first hole element 113Y is lower than 2.5 V in Step 2 (ST2).

In Step 2, when the output of the first hole element 113Y is smaller than 2.5 V, in step 12 the position of the liquid surface is set to a value that is acquired from the first table as a distance corresponding to the output of the first hole element 113Y (ST12), and the process ends. On the other hand, when the output of the first hole element 113Y is higher than 2.5 V in Step 2, in Step 3, it is determined whether the output of the second hole element 114Y is 2.5 V with the output of the first hole element 113Y being higher than 2.5 V (ST3).

When the condition in Step 3 is satisfied, in Step 13, the position of the liquid surface is set as a value acquired from adding 10 mm to a value acquired from the second table as a distance corresponding to the output of the first hole element 113Y (ST13), and the process ends. On the other hand, when the condition in Step 3 is not satisfied, in Step 4, it is determined whether the output of the first hole element 113Y is higher than 2.5 V (ST4).

When the condition in Step 4 is satisfied, in Step 14, the position of the liquid surface is set as a value acquired by adding 20 mm to a value acquired from the third table as a distance corresponding to the output of the first hole element 113Y (ST14), and the process ends. On the other hand, when the condition in Step 4 is not satisfied, in Step 5, it is determined whether the output of the second hole element 114Y is lower than 2.5 V (ST5).

When the condition in Step 5 is satisfied, in Step 15, the position of the liquid surface is set as a value acquired by adding 30 mm to a value acquired from the first table as a distance corresponding to the output of the second hole element 114Y (ST15), and the process, ends. On the other hand, when the condition in Step 5 is not satisfied, in Step 6, it is determined whether the output of the third hole element 115Y is 2.5 V with the output of the second hole element 114Y being higher than 2.5 V (ST6).

When the condition in Step 6 is satisfied, in Step 16, the position of the liquid surface is set as a value acquired by adding 40 mm to a value acquired from the second table as a distance corresponding to the output of the second hole element 114Y (ST16), and the process ends. On the other hand, when the condition in Step 16 is not satisfied, in Step 7, it is determined whether the output of the second hole element 114Y is higher than 2.5 V (ST7).

When the condition in Step 7 is satisfied, in Step 17, the position of the liquid surface is set as a value acquired by adding 50 mm to a value acquired from the third table as a distance corresponding to the output of the second hole element 114Y (ST17), and the process ends. On the other hand, when the condition in Step 7 is not satisfied, in Step 8, it is determined whether the output of the third hole element 115Y is lower than 2.5 V (ST8).

When the condition in Step 8 is satisfied, in Step 18, the position of the liquid surface is set as a value acquired by adding 60 mm to a value acquired from the first table as a distance corresponding to the output of the third hole element 115Y (ST18), and the process ends. On the other hand, when the condition in Step 8 is not satisfied, in Step 9, it is determined whether the output of the second hole element 114Y is 2.5 V with the output of the third hole element 115Y being higher than 2.5 V (ST9).

When the condition in Step 9 is satisfied, in Step 19, the position of the liquid surface is set as a value acquired by adding 70 mm to a value acquired from the third table as a distance corresponding to the output of the third hole element 115Y (ST19), and the process ends. On the other hand, when the condition in Step 9 is not satisfied, in Step 10, an error is determined (ST10), and the process ends.

Figure 17:
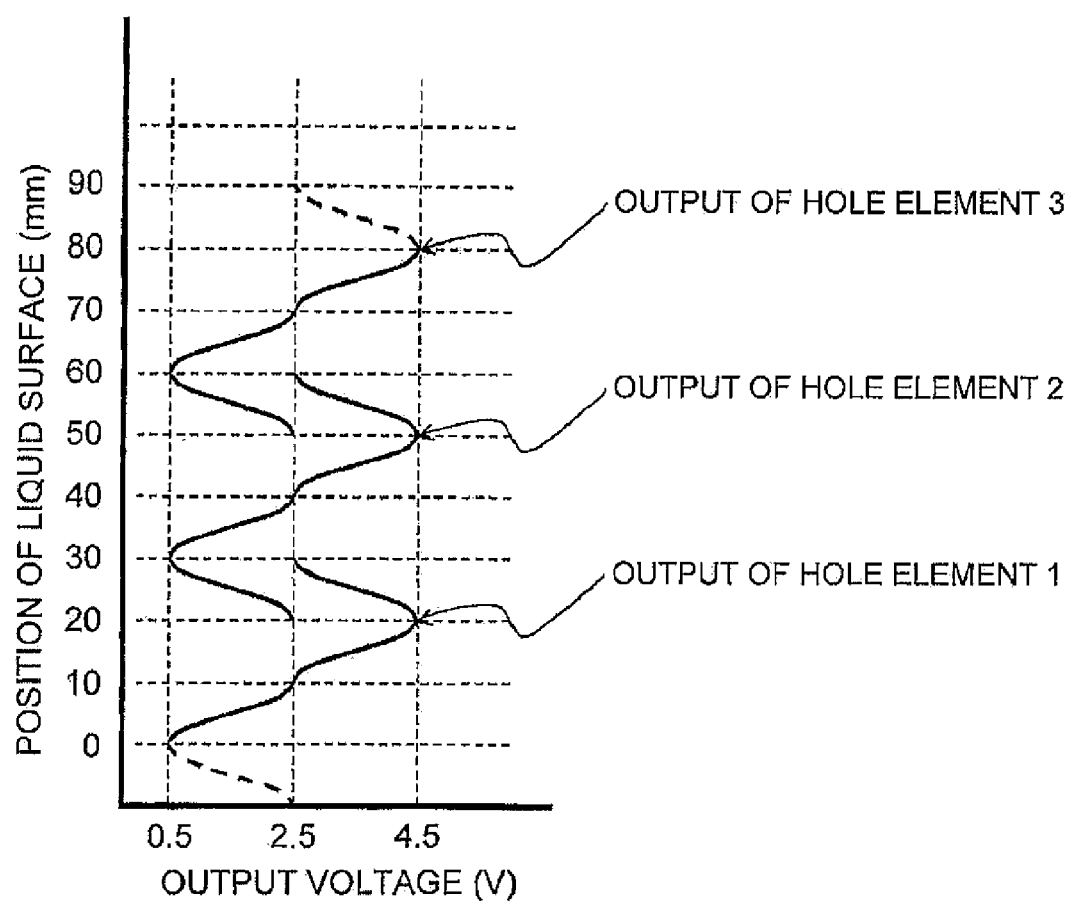
FIG. 17 is a diagram showing the result acquired from performing the process of the flowchart shown in FIG. 16.

FIG. 17 is a diagram showing the result acquired from performing the process of the flowchart shown in FIG. 16. As shown in FIG. 17, the position of the liquid surface corresponding to the outputs of the hole elements 113Y, 114Y, and 115Y is acquired.

According to the above-described liquid-level detecting unit 110Y, the number of components is decreased and costs are kept low. In addition, a long distance can be detected, and halt of the system can thereby be suppressed.

Control of the developer pump 76Y and the carrier liquid pump 79Y is now described. The developer pump 76Y and the carrier liquid pump 79Y are controlled based on shortages of the amount of toner or the amount of the carrier liquid contained in the liquid developer.

First, the amount of toner contained in the liquid developer and the amount of the carrier liquid are calculated by using the liquid-level detecting unit 110Y and the density measuring device 120Y shown in FIG. 14. Then, shortages of the amounts of toner and the carrier liquid contained in the liquid developer for object values that are stored in advance are calculated.

Figure 18:
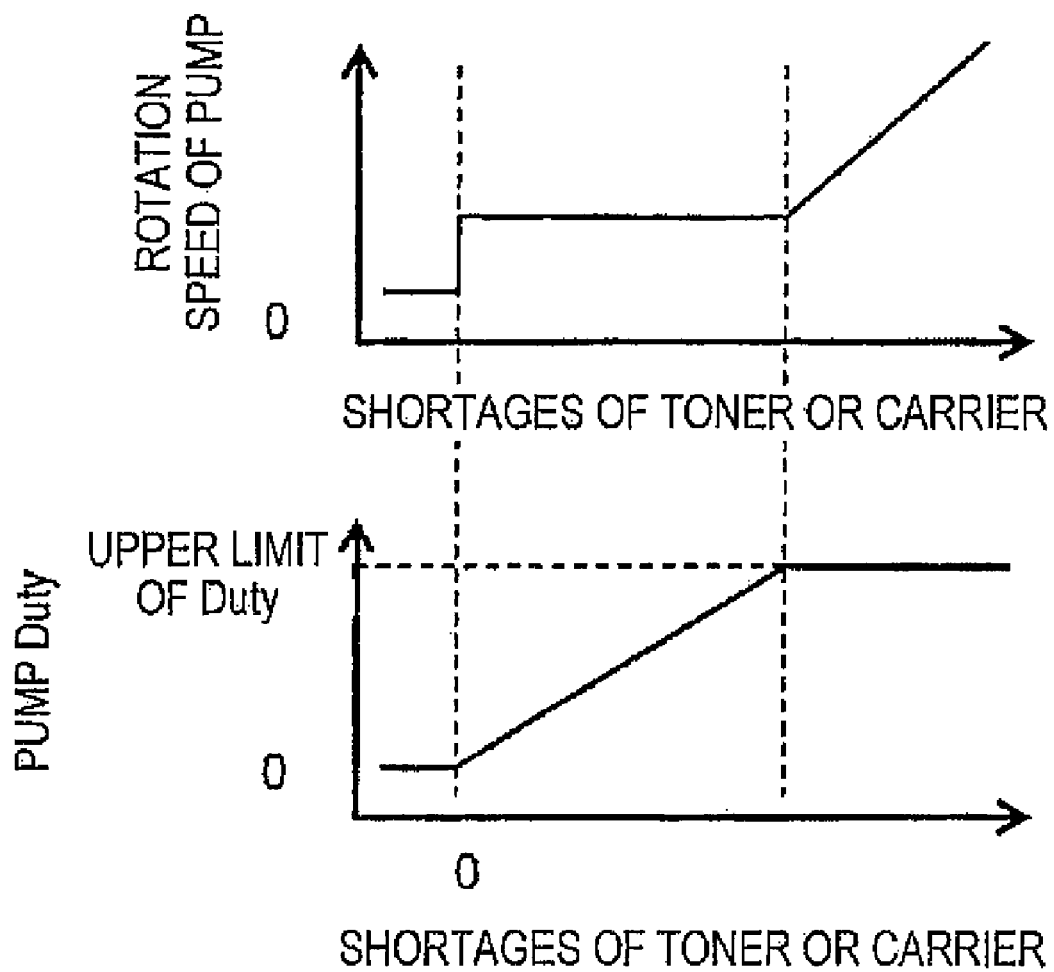
FIG. 18 is a diagram showing rotation speeds and duty values of a developer pump and a carrier liquid pump for shortages of the amount of toner or the amount of the carrier liquid according to an embodiment of the invention.

FIG. 18 is a diagram showing rotation speeds and duty values of the developer pump 76Y and the carrier liquid pump 79Y for shortages of the amount of toner or the amount of the carrier liquid. As shown in FIG. 18, the developer pump 76Y and the carrier liquid pump 79Y have constant rotation speeds up to the upper limits of the duty values, and the duty values thereof are changed in accordance with the amount of shortages. After the upper limits of the duty values are reached, the numbers of rotations are increased in accordance with the amounts of shortages.

Figure 19:
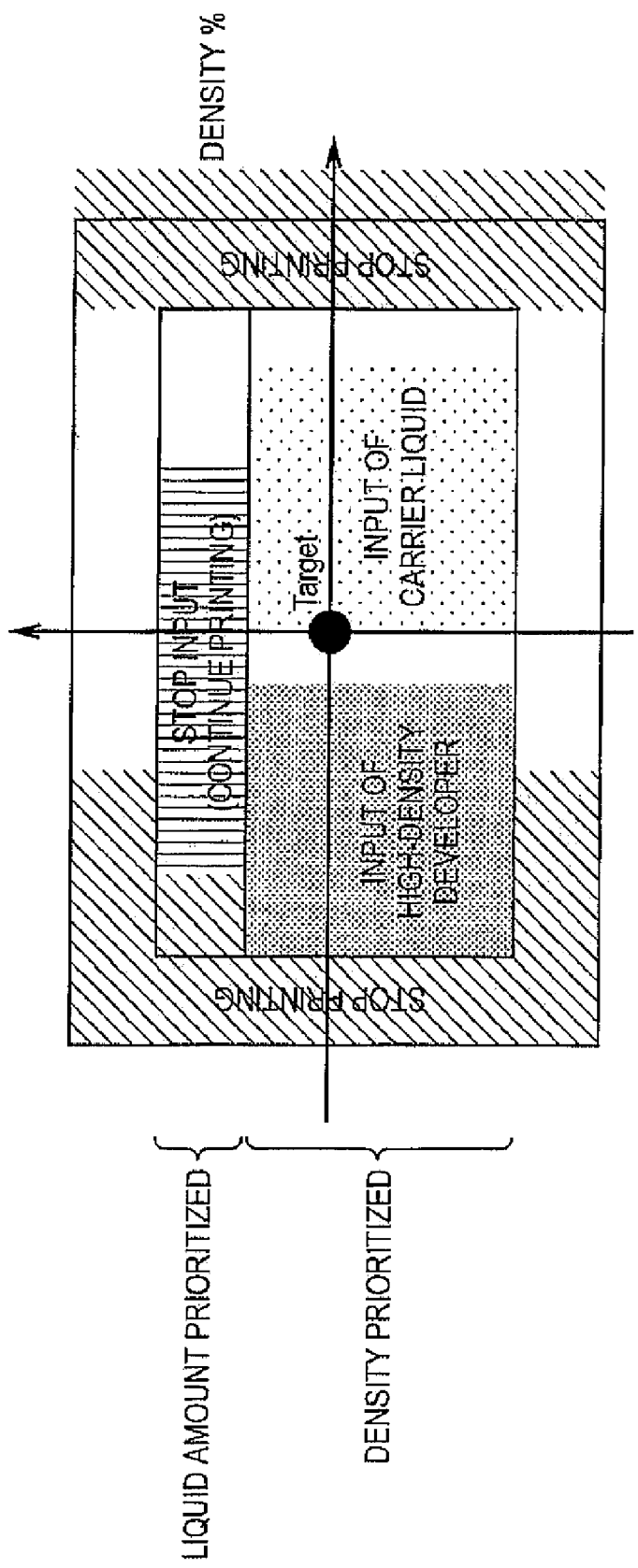
FIG. 19 is a diagram showing priorities of control for the amount and density of the liquid developer inside a liquid developer storing unit according to an embodiment of the invention.

A control process for priority of control in a printing state is now described. FIG. 19 is a diagram showing priorities of control for the amount and density of the liquid developer inside the liquid developer storing unit 71Y.

As shown in FIG. 19, the density is prioritized with respect to the liquid amount of up to a certain degree. On the other hand, when the liquid amount exceeds the certain degree, the liquid amount is prioritized.

For example, up to a liquid amount of a certain degree, the density is prioritized. Thus, when the density is high, the carrier liquid is input from the carrier liquid tank 77Y to the liquid developer storing unit 71Y. On the other hand, when the density is low, high-density developer is input from the developer tank 74Y to the liquid developer storing unit 71Y. In a case where the liquid amount is prioritized, when the liquid amount is large and exceeds a threshold value, input of the carrier liquid and the high-density developer is stopped regardless of the density and printing is continued. However, when the density or the liquid amount is beyond a specific range, printing is stopped.

The speeds of the developer compressing roller 22Y and the developer supplying roller 32Y may be controlled in accordance with the detected density so as to control the density of the developer in the developing nip.

Figure 20:
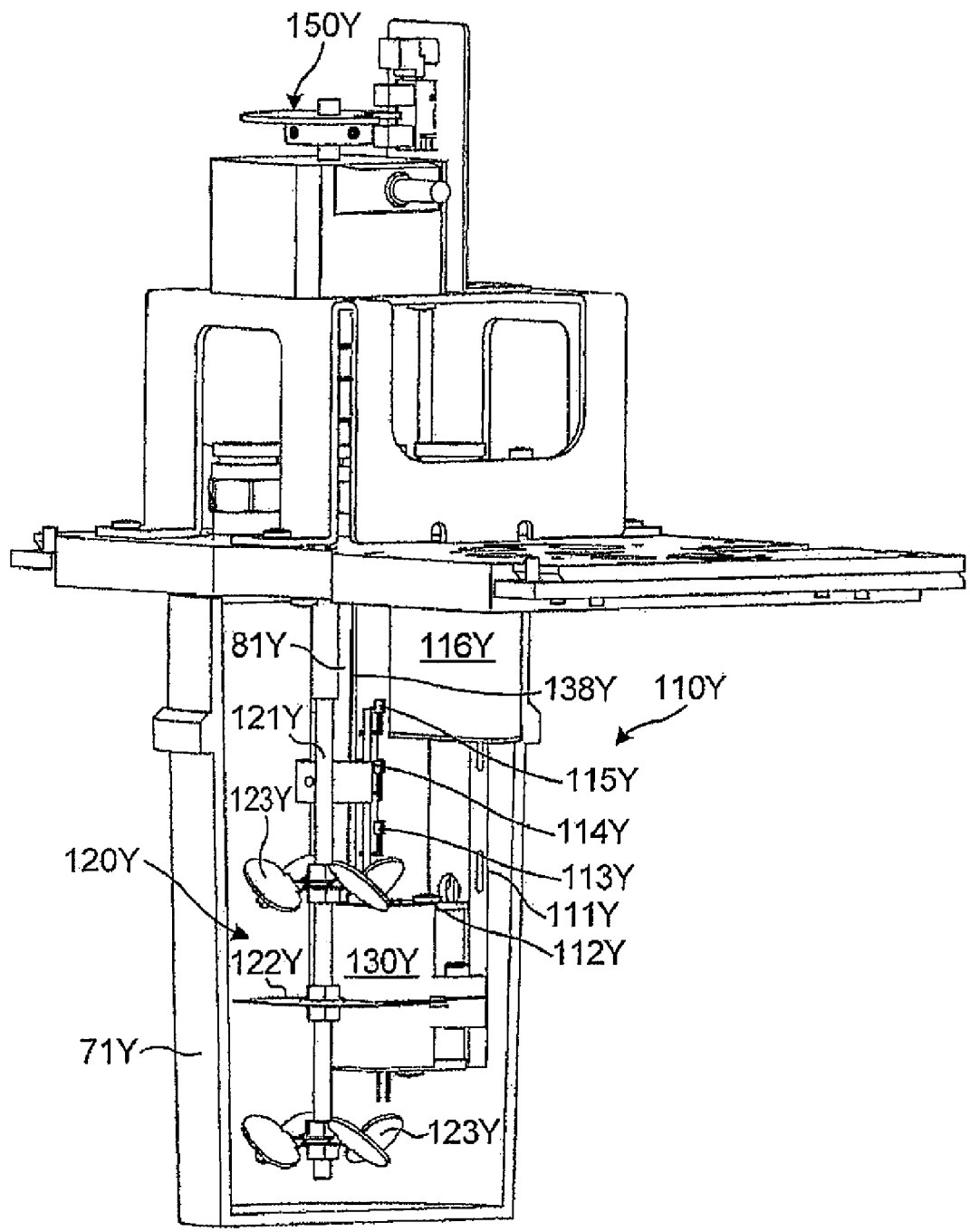
FIG. 20 is a perspective view of a liquid developer storing unit according to another embodiment of the invention.
Figure 21:
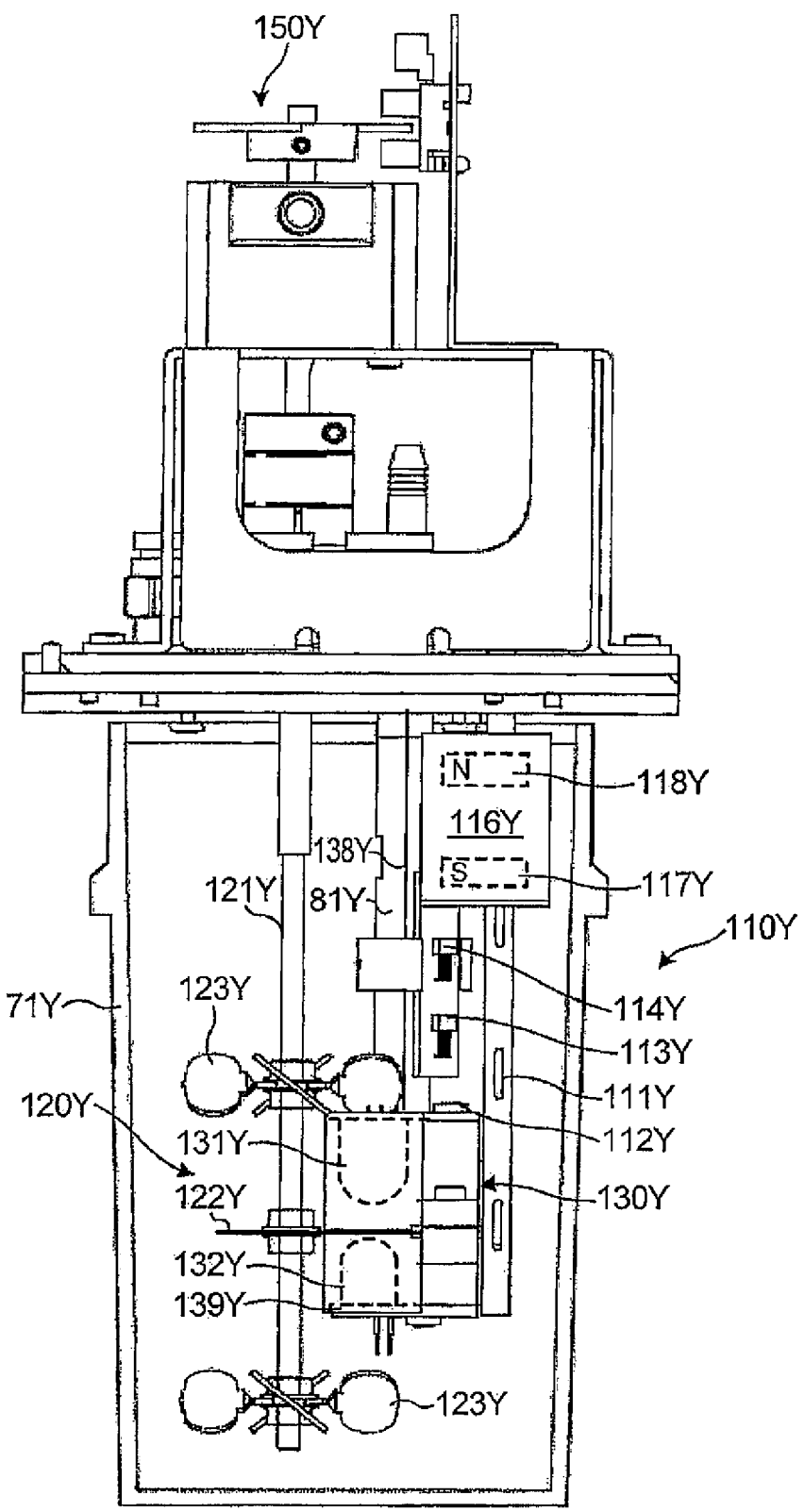
FIG. 21 is a cross-sectional view of a liquid developer storing unit according to another embodiment of the invention.
Figure 22:
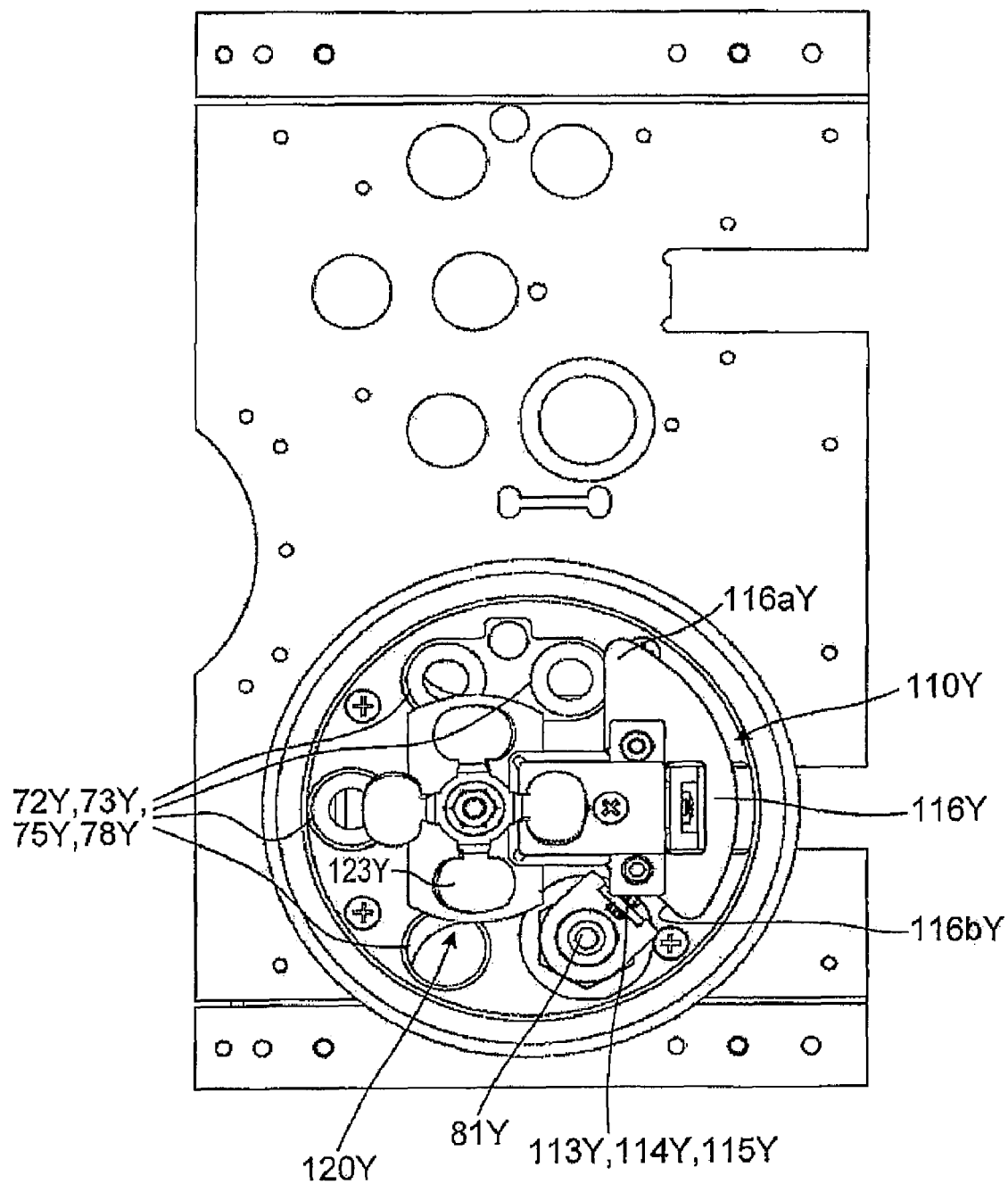
FIG. 22 is a diagram of a liquid developer storing unit according to another embodiment of the invention, viewed from the lower side.
Figure 23:
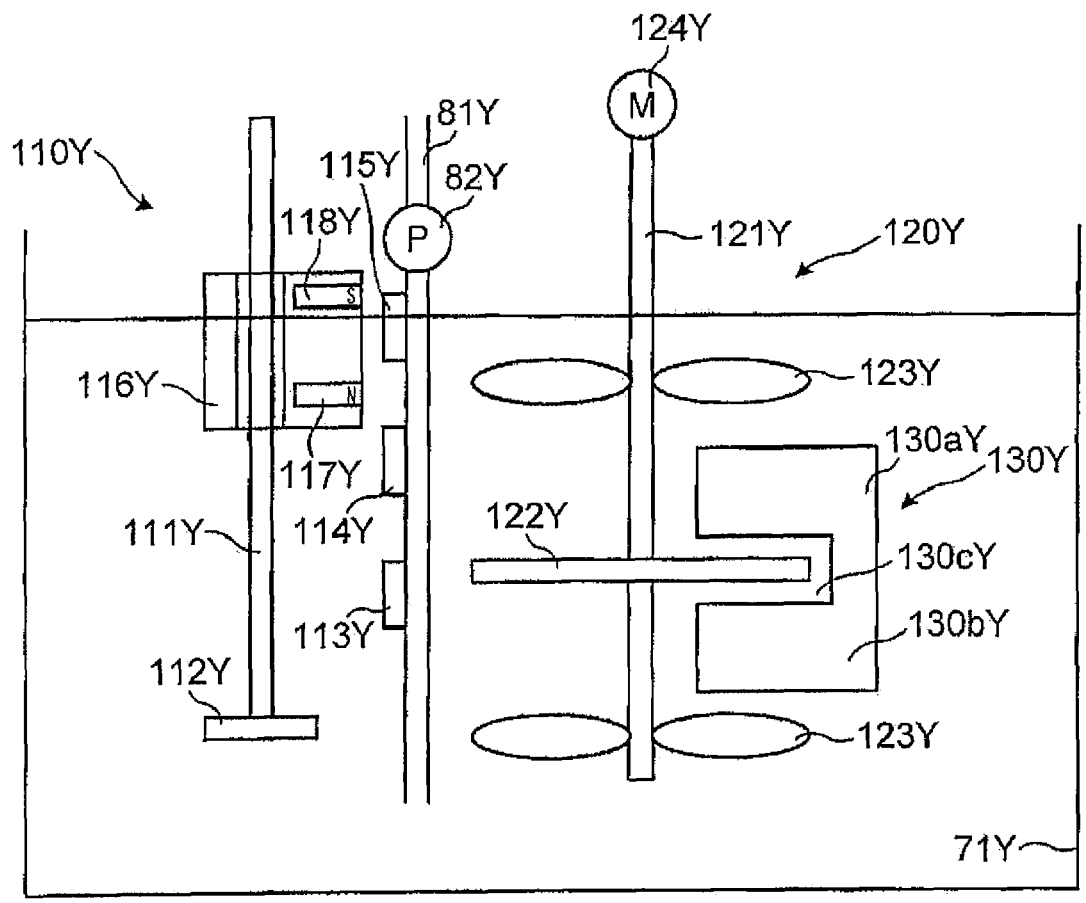
FIG. 23 is schematic diagram of a liquid developer storing unit according to another embodiment of the invention.

FIGS. 20-23 are diagrams showing a liquid-level detecting unit 110Y and a density measuring device 120Y, located inside the liquid developer storing unit 71Y, according to another embodiment of the invention. FIG. 20 is a perspective view of a liquid developer storing unit according to another embodiment of the invention. FIG. 21 is a cross-sectional view of a liquid developer storing unit according to another embodiment of the invention. FIG. 22 is a diagram of a liquid developer storing unit according to another embodiment of the invention, viewed from the lower side. FIG. 23 is a schematic diagram of a liquid developer storing unit according to another embodiment. The liquid-level detecting unit 110Y and the density measuring device 120Y, located inside the liquid developer storing unit 71Y measure the liquid level and the density of the liquid developer, as shown in FIG. 10. In this embodiment, the first hole element 113Y, the second hole element 114Y, and the third hole element 115Y are disposed in the developer supplying path 81Y used for supplying the liquid developer from the liquid developer storing unit 71Y to a supply unit 31bY of the developer container 31Y.

First, the liquid-level detecting unit 110Y as a liquid level sensor is described. The liquid-level detecting unit 110Y has a float supporting member 111Y, a regulating member 112Y, a first hole element 113Y, a second hole element 114Y, and a third hole element 115Y that are examples of proportional output-type hole elements, a float 116Y as an example of a floating member, and first and second magnetic field generators 117Y and 118Y.

The float supporting member 111Y supports the float 116Y to be movable from a position on the liquid surface inside the liquid developer storing unit 71Y of yellow to a measurable position below the liquid surface. The regulating member 112Y is disposed in the density measuring unit 130Y of the density measuring device 120Y and prevents interferences of the float 116Y and the density measuring unit 130Y.

The first hole element 113Y, the second hole element 114Y, and the third hole element 115Y are sequentially disposed from the lower side with a predetermined distance apart from the developer supplying path 81Y through a bracket or the like.

The first hole element 113Y, the second hole element 114Y, and the third hole element 115Y are formed of proportional output-type hole elements of which output voltage changes in accordance with magnetic flux density. In this embodiment, the distance between the hole elements is set to 30 mm.

The float 116Y is a member that is movable relative to the float supporting member 111Y by floating on the liquid surface in accordance with the position of the liquid surface. On the lower side of the float 116Y, the first magnetic field generator 117Y is disposed, and the second magnetic field generator 118Y is disposed on the upper side thereof to be a predetermined distance apart from the first magnetic field generator 117Y. The first magnetic field generator 117Y and the second magnetic field generator 118Y are disposed to be moved in accordance with movement of the float 116Y with facing the hole elements 113Y, 114Y, and 115Y. The first magnetic field generator 117Y and the second magnetic field generator 118Y are disposed to have the north (N) pole and the south (S) pole disposed on opposite sides to each other. In this embodiment, the first magnetic field generator 117Y faces its south (S) pole toward the hole elements 113Y, 114Y, and 115Y, and the second magnetic field generator 117Y faces its north (N) pole toward the hole elements 113Y, 114Y, and 115Y. The magnetic field generators 117Y and 118Y have a diameter of 5 mm, a length of 6 mm, and 4000 Gauss, and are spaced apart by 20 mm.

When the liquid surface of the liquid developer changes, the float 116Y is moved, and accordingly, distances between the first and second magnetic field generators 117Y and 118Y and the hole elements 113Y, 114Y, and 115Y are changed. In accordance with the changes in the distances, magnetic fields detected by the hole elements 113Y, 114Y, and 115Y change, and thus, it is possible to acquire the liquid level based on the detected values of the hole elements 113Y, 114Y, and 115Y.

The density measuring device 120Y has an agitating propeller shaft 121Y, a transparent propeller 122Y as an example of a moving member, an agitating propeller 123Y as an example of an agitating member, and a density measuring unit 130Y. The transparent propeller 122Y and the agitating propeller 123Y are disposed on a same shaft (the agitating propeller shaft 121Y), and the agitating propeller shaft 121Y is a member that is rotated by a motor 124Y.

Since the structure of the density measuring unit 130Y is almost the same as that shown in FIGS. 11 and 12, a description of a same element will be omitted here.

The density measuring unit 130Y has a case formed of an insulating member such as plastic. The case has a gap 130cY, and the transparent propeller 122Y is supported by the agitating propeller shaft 121Y and is formed of a member having a flat plate shape such as a rectangle that can be rotatable. The transparent propeller 122Y has a structure for intermittently passing a gap 130cY between first and second members 130aY and 130bY of the density measuring unit 130Y. The first member 130aY or the second member 130bY can be moved, and thus a distance of the gap 130cY can be changed. The distance of the gap 130cY may be changed in accordance with the color of the liquid developer.

The density measuring unit 130Y has a light emitting diode (LED) 131Y, a density-measuring light receiving element 132Y, a emission intensity-measuring light receiving element 133Y, and the like, and wirings 138Y thereof are disposed in the developer supplying path 81Y. The density-measuring light receiving element 132Y, the emission intensity-measuring light receiving element 133Y, and the like are supported by a metal plate 139Y that is electrically floating, and accordingly, electrical influence on the density measuring unit 130Y can be reduced.

In addition, the liquid-level detecting unit 110Y and the density measuring device 120Y have a height adjusting mechanism 150Y that can adjust a height on the whole. Thus, the whole position can be adjusted, and accordingly, the degree of design freedom is increased.

As shown in FIG. 22, when this embodiment is viewed from the lower side, the agitating propeller 123Y is rotated in the clockwise direction and is overlapped with at least one of openings of the developing unit collecting path 72Y, the image carrier collecting path 73Y, the developer supplying path 75Y, and the carrier liquid supplying path 78Y. Accordingly, newly collected or supplied liquid developer can be agitated in a speedy manner.

In addition, the float 116Y has a fan-shaped section, and an end part 116aY of the float 116Y opposite to the hole elements 113Y, 114Y, and 115Y has a rounded acute-angled shape to enable the liquid developer to flow in an easy manner. In addition, a face 116bY of the float 116Y opposite to the end part 116aY faces the hole elements 113Y, 114Y, and 115Y. Accordingly, the flow of the liquid developer is reduced, and the precision of the hole elements 113Y, 114Y, and 115Y is improved.

Figure 24:
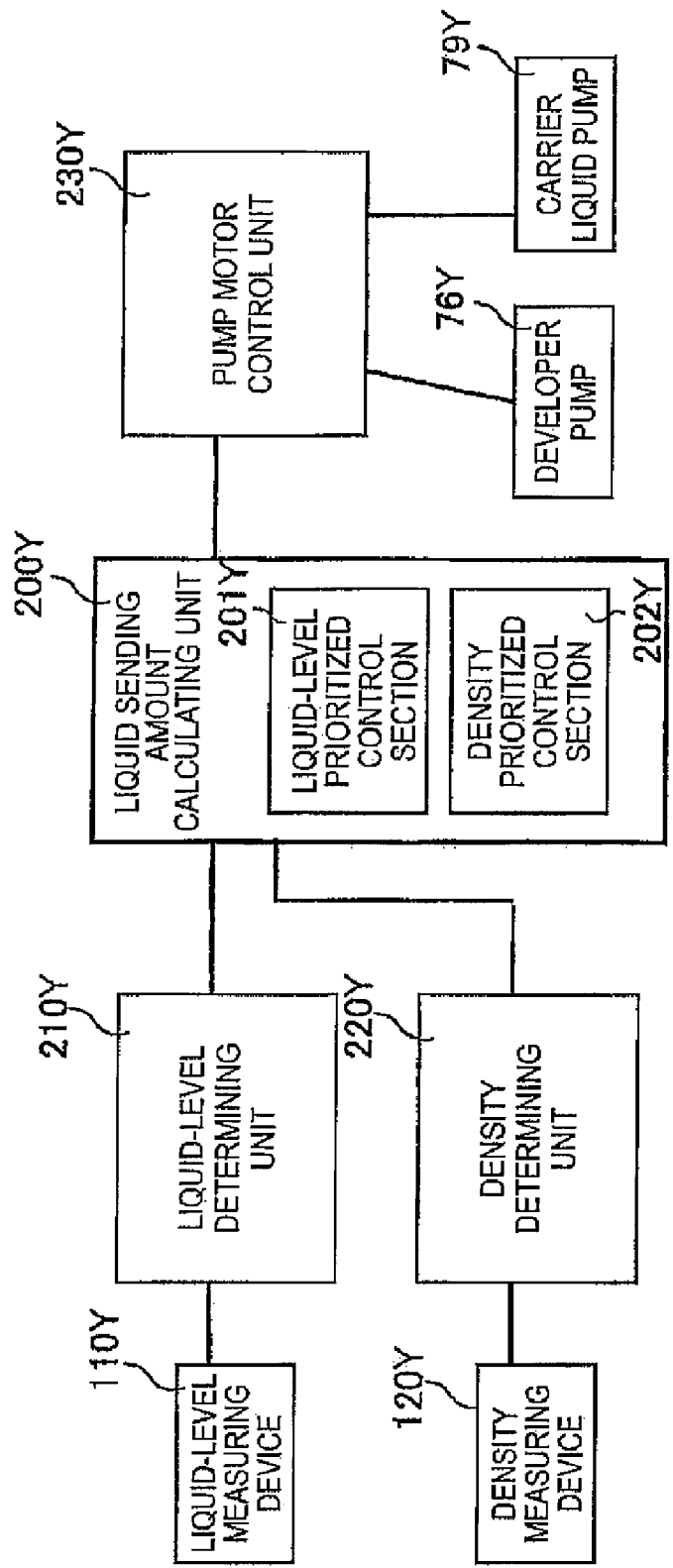
FIG. 24 is a block diagram showing a relationship of a liquid-level detecting unit, a density measuring device, and a developer collecting and supplying device according to an embodiment of the invention.

FIG. 24 is a block diagram showing a relationship of the liquid-level detecting unit 110Y, the density measuring device 120Y, and the developer collecting and supplying device 70Y according to an embodiment of the invention.

A liquid level determining unit 210 determines whether the liquid level measured by the liquid-level detecting unit 110Y is higher than a predetermined level. When the liquid level determining unit 210 determines that the liquid level measured by the liquid-level detecting unit 110Y is higher than the predetermined level, a liquid sending amount calculating unit 200 sets the liquid amount prioritizing mode and outputs a signal from a liquid-level priority control section 201 to a pump motor control unit 230 to prohibit input of the liquid developer. The pump motor control unit 230 prohibits operation of pump motors such as the developer pump 76Y, the carrier liquid pump 79Y, and the like to prohibit input of the liquid developer. Accordingly, an overflow and the like can be eliminated.

In addition, it is determined whether the density measured by the density measuring device 120Y is higher than a first or second predetermined density by the density determining unit 220. When the density determining unit 220 determines that the density measured by the density measuring device 120Y is higher than the first predetermined density or is lower than the second predetermined density that is set to be lower than the first predetermined density, the density determining unit 220 sets the density prioritized mode and stops printing by using a density priority control section 202. Accordingly, an image is not formed with a deteriorated image quality.

Figure 25A:
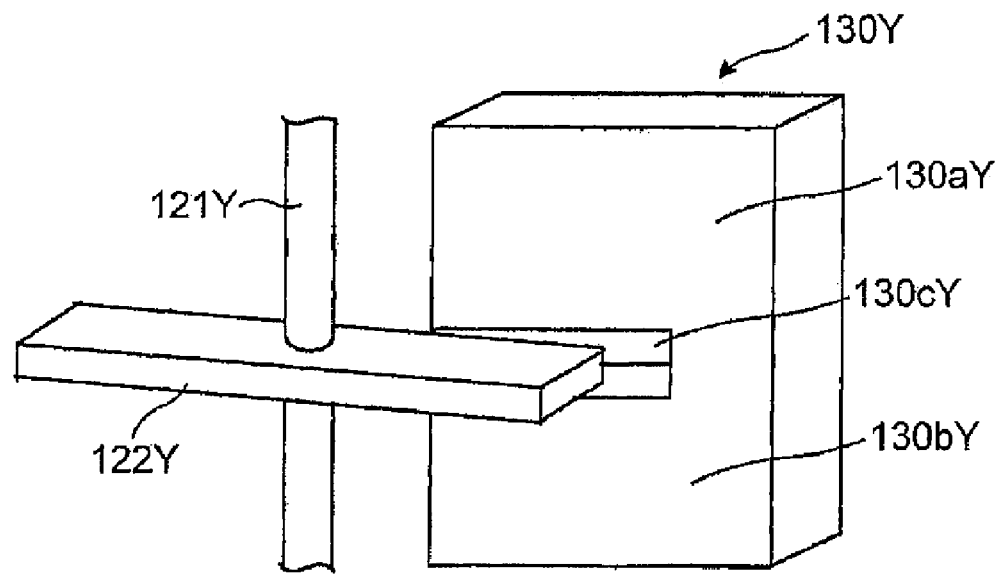
FIGS. 25A and 25B are diagrams showing a relationship between a transparent propeller and a density measuring unit according to an embodiment of the invention.
Figure 25B:
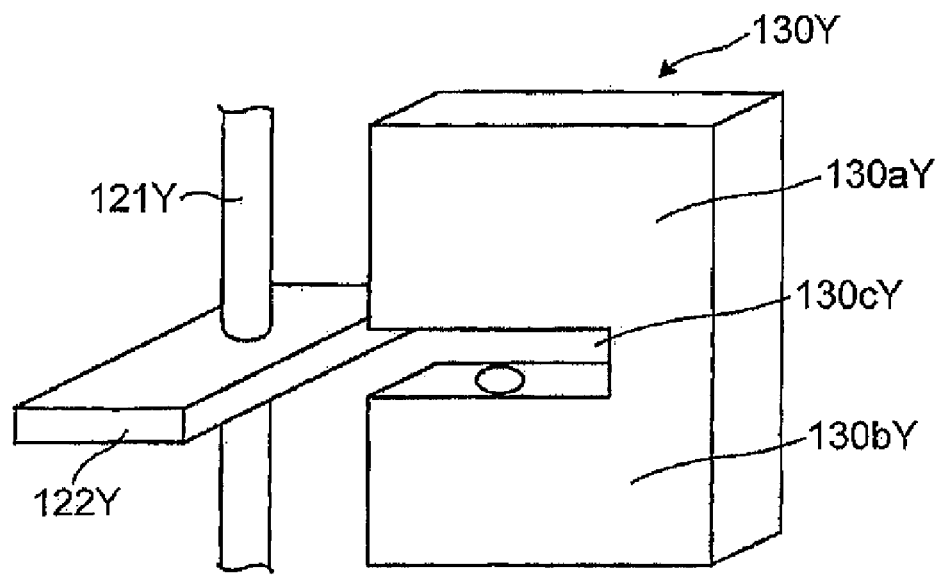

FIGS. 25A and 25B are diagrams showing a relationship between the transparent propeller 122Y and the density measuring unit 130Y. FIG. 25A is a diagram showing a state just before the transparent propeller 122Y is inserted into the gap 130cY of the density measuring unit 130Y. FIG. 25B is a diagram showing a state that the transparent propeller 122Y is moved out of the gap 130cY of the density measuring unit 130Y.

As shown in FIG. 25, the transparent propeller 122Y is formed of a member having a flat plate shape such as a rectangle that is supported by the agitating propeller shaft 121Y, which is the same shaft as that of the agitating propeller 123Y, to be perpendicular to the agitating propeller shaft 121Y and can be rotated. The transparent propeller 122Y has a structure for intermittently passing a sensing area inside the gap 130cY of the density measuring unit 130Y. The transparent propeller 122Y may further include a width adjusting member that adjusts the width of the gap 130cY. The distance of the gap 130cY may be configured to change in accordance with the color of the liquid developer. In addition, the first member 130aY and the second member 130bY may be divided to configure a movable structure.

In accordance with rotation of the agitating propeller shaft 121Y, the transparent propeller 122Y, as shown in FIG. 25A, repeats a state in which an edge of the transparent propeller 122Y is positioned between the light emitting diode LED 131Y and the density-measuring light receiving element 132Y such as a photo interrupter for starting light shielding, a state in which an opposite edge is positioned in the sensing area between the light emitting diode LED 131Y and the density-measuring light receiving element 132Y for completing light shielding, and a state, as shown in FIG. 25B, in which the transparent propeller 122Y is not positioned between the light emitting diode LED 131Y and the density-measuring light receiving element 132Y. The density-measuring light receiving element 132Y outputs High and Low signals in accordance with a light-shielded state and a non light-shielded state.

The agitating propeller shaft 121Y is rotated at about 300 rpm by a motor 124Y. The transparent propeller 122Y is fixed to the agitating propeller shaft 121Y. Accordingly, when a time interval of 20-120 ms elapses after the output signal of the density-measuring light receiving element 132Y is switched from Low to High, the transparent propeller 122Y is positioned between the light emitting diode (LED) 131Y and the density-measuring light receiving element 132Y so as to shield light completely. In addition, when a time interval of 70-170 ms elapses after the output signal of the density-measuring light receiving element 132Y is switched from Low to High, the transparent propeller 122Y is not positioned between the light emitting diode LED 131Y and the density-measuring light receiving element 132Y, and a state in which light is not completely shielded is formed. By the above-described operation, when the output signal of the density-measuring light receiving element 132Y is switched from Low to High, the density measuring device 120Y counts the time interval and reads in a signal from the density measuring unit 130Y at a time when a predetermined time elapses.

In addition, according to an embodiment of the invention, the liquid developer storing device is configured by the density measuring device 120Y, the storing unit 71Y, and the like.

As described above, the density measuring device according to this embodiment has the transparent propeller 122Y that can be moved in a liquid, the light emitting diode (LED) 131Y, the density-measuring light receiving element 132Y that receives light emitted by the light emitting diode (LED) 131Y, the gap 130cY in which the transparent propeller 122Y disposed in a light path from the light emitting diode (LED) 131Y can be moved, and the density measuring unit 130Y that measures the density of the liquid based on the result of the output of the density-measuring light receiving element 132Y for cases where the transparent propeller 122Y is disposed in the light path from the light emitting diode (LED) 131Y and the transparent propeller 122Y is not located in the light path from the light emitting diode (LED) 131Y. Accordingly, the liquid does not need to be pumped to the density measuring unit 130Y by using a pump or the like, and the number of components can be decreased. In addition, since the transparent propeller 122Y is moved in the gap 130cY, a new liquid can come into the gap 130cY, and accordingly, the precision of density measurement is improved.

In addition, the light emitting diode (LED) 131Y is disposed on the first side of the gap 130cY, and the density-measuring light receiving element 132Y is disposed on the second side of the gap 130cY, and accordingly, the precision of density measurement is improved further.

In addition, the light emitting diode (LED) 131Y and the density-measuring light receiving element 132Y are disposed on the first side of the gap 130cY and the reflective member that reflects light from the light emitting diode (LED) 131Y to the density-measuring light receiving element 132Y is disposed on the second side of the gap 130cY. Thus, the light emitting diode (LED) 131Y and the density-measuring light receiving element 132Y are disposed on the same side, and accordingly, work efficiency is improved.

In addition, since the transparent propeller 122Y passes through the light path of the light emitted from the light emitting diode (LED) 131Y intermittently, the density can be measured more precisely.

In addition, since the transparent propeller 122Y is a rotary member, a transparent propeller having a simple structure is moved into the gap 130cY.

In addition, since the transparent propeller 122Y has a rectangular shape, a new liquid can be inserted into the gap 130cY by using a simple structure.

In addition, since the agitating member has the same shaft as that of the transparent propeller 122Y and agitates the liquid developer, the number of parts is decreased.

In addition, the first member 130aY disposed on the first side that covers the light emitting diode LED 131Y and the second member 130bY that covers the density-measuring light receiving element 132Y disposed on the second side are separately formed, and the gap 130cY is constituted by the first member 130aY and the second member 130bY. Accordingly, a measuring process appropriate for the type or state of a liquid can be performed.

In addition, since the width adjusting member that adjusts the width of the gap 130cY is provided, a measuring process more appropriate for the type or state of a liquid can be performed.

In addition, since the emission intensity-measuring light receiving element 133Y receives light emitted from the light emitting diode (LED) 131Y in a light path that does not pass through the transparent propeller 122Y, the precision of density measurement is further improved.

In addition, the liquid developer storing device according to an embodiment of the invention has the storage unit in which the liquid developer is stored, and the density measuring device including the transparent propeller 122Y that can be moved in the storage the unit, the light emitting diode (LED) 131Y, the density-measuring light receiving element 132Y that receives light emitted by the light emitting diode (LED) 131Y, the gap 130cY in which the transparent propeller 122Y disposed on the path of light emitted from the light emitting diode (LED) 131Y can be moved, and the density measuring unit 130Y that measures the density of the liquid developer based on the result of output of the density-measuring light receiving element 132Y for cases where the transparent propeller 122Y is in the light path of light emitted from the light emitting diode (LED) 131Y and the transparent propeller 122Y is not in the light path of light emitted from the light emitting diode (LED) 131Y. Accordingly, the precision of density measurement is improved and it is possible to precisely adjust the liquid developer to have a needed density.

In addition, the image forming apparatus according to an embodiment of the invention includes a developer container 31Y, a developer carrier 20Y that carries the liquid developer, the developer supplying member 32Y that supplies liquid developer stored in the developer container 31Y to the developer carrier 20Y, the image carrier 10Y on which a latent image is formed by the developer carrier 20Y, the transfer body 40 that forms an image by transferring the image formed on the image carrier 10Y, the storage unit in which the liquid developer is stored, the developer collecting and supplying device 70Y that collects the liquid developer from the developer container 31Y into the storage unit and supplies the liquid developer and the carrier liquid, and the density measuring device including the transparent propeller 122Y that can be moved inside the storage unit, the light emitting diode (LED) 131Y, the density-measuring light receiving element 132Y that receives light emitted by the light emitting diode (LED) 131Y, the gap 130cY in which the transparent propeller 122Y disposed in the light path from the light emitting diode (LED) 131Y can be moved, and the density measuring unit 130Y that measures the density of the liquid based on the result the output of the density-measuring light receiving element 132Y for cases where the transparent propeller 122Y is disposed in the light path from the light emitting diode (LED) 131Y and the transparent propeller 122Y is not located in the light path from the light emitting diode (LED) 131Y. Accordingly, the precision of density measurement is improved, and the liquid developer can be precisely adjusted to have a needed density. Therefore, an image with high image quality can be formed.

In addition, since the supply path 81Y that supplies the liquid developer from the liquid developer storing unit 71Y to the developer container 31Y is included and the wiring 138Y of the density measuring device is disposed along the supply path 81Y, the number of components is decreased, and the wiring 138Y can be stably maintained.

In addition, the collecting paths 72Y, 73Y, 75Y, and 78Y that collect the liquid developer into the liquid developer storing unit 71Y, the agitating propeller 123Y that agitates the liquid developer inside the liquid developer storing unit 71Y, and the agitating propeller shaft 121Y that supports the agitating propeller 123Y to be rotatable are provided, and the agitating propeller 123Y overlaps the collecting paths 72Y, 73Y, 75Y, and 78Y when viewed from the direction of the agitating propeller shaft 121Y. Accordingly, newly collected or supplied liquid developer can be agitated in a speedy manner.

What is claimed is:

1. A density measuring device comprising:
   a transparent moving member configured to move in a liquid;
   a light emitting member;
   a light receiving member that receives light emitted by the light emitting member;
   a gap part in which the moving member disposed in a path of light emitted from the light emitting member can be moved; and
   a density measuring unit that measures the density of the liquid based on a result of output of the light receiving member for a case where the moving member is located in the path of light emitted from the light emitting member, wherein the light passes through the moving member, and a case where the moving member is not located in the path of light emitted from the light emitting member.

2. The density measuring device according to claim 1, wherein
   the light emitting member is disposed on a first side of the gap part, and
   the light receiving member is disposed on a second side of the gap part.

3. The density measuring device according to claim 1, wherein
   the light emitting member and the light receiving member are disposed on the first side of the gap part, and
   a reflective member that reflects the light emitted from the light emitting member to the light receiving member is disposed on the second side of the gap part.

4. The density measuring device according to claim 1, wherein the moving member intermittently passes through the path of light emitted from the light emitting member.

5. The density measuring device according to claim 1, wherein the moving member is a rotary member.

6. The density measuring device according to claim 5, further comprising:
an agitating member that has a same shaft as that of the moving member and agitates liquid developer.

7. The density measuring device according to claim 1, wherein the moving member is in the shape of a rectangle.

8. The density measuring device according to claim 1, further comprising:
a first member that covers the light emitting member and is disposed on the first side; and
a second member that covers the light receiving member, formed separately from the first member, and is disposed on the second side,
wherein the gap part is configured by the first member and the second member.

9. The density measuring device according to claim 1, further comprising:
a second light receiving member that receives the light emitted from the light emitting member in a light path that does not pass through the moving member.

10. A liquid developer storing apparatus comprising:
a storage unit in which liquid developer is stored; and
a density measuring device including:
a transparent moving member configured to move in the storage unit;
a light emitting member;
a light receiving member that receives light emitted by the light emitting member;
a gap part in which the moving member disposed in a path of light emitted from the light emitting member can be moved; and
a density measuring unit that measures the density of the liquid based on a result of output of the light receiving member for a case where the moving member is located in the path of light emitted from the light emitting member, wherein the light passes through the moving member, and a case where the moving member is not located in the path of light emitted from the light emitting member.

11. An image forming apparatus comprising:
a developer container;
a developer carrier that carries liquid developer;
a developer supplying member that supplies the liquid developer stored in the developer container to the developer carrier;
an image carrier on which a latent image is developed by the developer carrier;
a transfer body that forms an image by transferring an image formed on the image carrier;
a storage unit in which the liquid developer is stored;
a developer collecting and supplying device that collects the liquid developer from the developer container into the storage unit and supplies the liquid developer and a carrier liquid; and
a density measuring device including:
a transparent moving member configured to move in the storage unit;
a light emitting member;
a light receiving member that receives light emitted by the light emitting member;
a gap part in which the moving member disposed in a path of light emitted from the light emitting member can be moved; and
a density measuring unit that measures the density of the liquid based on a result of output of the light receiving member for a case where the moving member is located in the path of light emitted from the light emitting member, wherein the light passes through the moving member, and a case where the moving member is not located in the path of light emitted from the light emitting member.

12. The image forming apparatus according to claim 11, further comprising:
a supply path through which the liquid developer is supplied from the storage unit of the liquid developer to the developer container,
wherein a wiring of the density measuring device is disposed along the supply path.

13. The image forming apparatus according to claim 11, further comprising:
a collecting path through which the liquid developer is collected into the storage unit of the liquid developer;
an agitating propeller that agitates the liquid developer inside the storage unit of the liquid developer; and
an agitating propeller shaft that supports the agitating propeller to be rotatable,
wherein the agitating propeller is overlapped with the collecting path, when viewed from the direction of the agitating propeller shaft.

* * * * *